(12) United States Patent
Mi et al.

(10) Patent No.: US 11,761,974 B2
(45) Date of Patent: Sep. 19, 2023

(54) CELL AND MEDICAMENT DISPENSING DEVICE FOR DRUG SCREENING AND METHOD THEREOF

(71) Applicant: DRSIGNAL BIOTECHNOLOGY CO., LTD., New Taipei (TW)

(72) Inventors: Hsin Wu Mi, New Taipei (TW); Hsin Fei Huang, New Taipei (TW)

(73) Assignee: DrSignal BioTechnology Co., Ltd., New Taipei (TW)

( * ) Notice: Subject to any disclaimer, the term of this patent is extended or adjusted under 35 U.S.C. 154(b) by 58 days.

(21) Appl. No.: 17/453,026

(22) Filed: Nov. 1, 2021

(65) Prior Publication Data
US 2023/0135251 A1    May 4, 2023

(51) Int. Cl.
*G01N 35/10* (2006.01)
*C12M 1/32* (2006.01)
(Continued)

(52) U.S. Cl.
CPC ......... *G01N 35/1065* (2013.01); *C12M 23/12* (2013.01); *C12M 25/06* (2013.01);
(Continued)

(58) Field of Classification Search
CPC ............... G01N 35/1065; G01N 35/04; G01N 2035/0425; C12M 23/12; C12M 25/06; C12M 33/06
See application file for complete search history.

(56) References Cited

U.S. PATENT DOCUMENTS

| 5,432,085 A | * 7/1995 | Warren ................. C12M 33/04 435/809 |
| 2002/0012611 A1 | 1/2002 | Stylli et al. |

(Continued)

FOREIGN PATENT DOCUMENTS

| CN | 102653730 A | 9/2012 |
| CN | 102653782 A | 9/2012 |
| WO | 2009034945 A1 | 3/2009 |

OTHER PUBLICATIONS

International Search Report Issued by Foreign Patent Office in Application No. EP21205920.8.

*Primary Examiner* — Samuel P Siefke
*Assistant Examiner* — Henry H Nguyen
(74) *Attorney, Agent, or Firm* — Rosenberg, Klein & Lee

(57) ABSTRACT

A cell and medicament dispensing device for drug screening is configured to dispense minute amount of cells and medicaments. The device has a base, a transfer plate serving mechanism, a transfer plate positioning mechanism, an injection mechanism, a cell culture plate positioning mechanism, and a dispensing mechanism. The transfer plate serving mechanism moves a transfer plate to the transfer plate positioning mechanism. The injection mechanism injects cells and medicaments into recesses in the transfer plate. A cell culture plate is fixed in the cell culture plate positioning mechanism. The dispensing mechanism moves back and forth between a position above the transfer plate and a position above the cell culture plate to dispense the cells or medicaments from the transfer plate to the cell culture plate. As a result, the process of drug screening is automated to reduce labor and improve quality significantly.

6 Claims, 38 Drawing Sheets

(51) Int. Cl.
  *C12M 1/12* (2006.01)
  *G01N 35/04* (2006.01)

(52) U.S. Cl.
  CPC ............ *C12M 33/06* (2013.01); *G01N 35/04* (2013.01); *G01N 2035/0425* (2013.01)

(56) References Cited

U.S. PATENT DOCUMENTS

| | | |
|---|---|---|
| 2002/0176803 A1 | 11/2002 | Hamel et al. |
| 2010/0330563 A1 | 12/2010 | Kodama et al. |
| 2011/0220239 A1 | 9/2011 | Reed et al. |
| 2014/0241946 A1* | 8/2014 | Self ................ G01N 35/04 422/65 |
| 2019/0195901 A1* | 6/2019 | Iwasaki ............ G01N 35/0099 |
| 2020/0191808 A1* | 6/2020 | Cook ............... G01N 35/04 |

* cited by examiner

US 11,761,974 B2

CELL AND MEDICAMENT DISPENSING DEVICE FOR DRUG SCREENING AND METHOD THEREOF

BACKGROUND OF THE INVENTION

1. Field of the Invention

The present invention relates to an automation equipment for biology and chemistry laboratories, especially to a device and a method configured to dispense minute amount of cells or minute amount of medicaments into different wells of a culture plate.

2. Description of the Prior Arts

To perform drug screening, first dispense minute amount of cells into wells of a culture plate where the cells are then cultivated for several days. When the cultivation is completed, manually prepare different kinds of medicament liquids in different containers, manually draw up and dispense precise amount of each medicament liquid into the wells with the cultivated cells one after another with a pipette.

However, a typical culture plate has dozens of wells, and there are several medicament liquids needed to be dispensed. As a result, simple and repetitive dispensing operation needs to be repeated for hundreds of times for each culture plate, making drug screening a long and laborious task.

Additionally, a disposable tip is mounted on a front end of the pipette, and the tip needs to be replaced before dispensing a different kind of cell or medicament liquid to prevent contamination. Replacement of the tip further increases the time and labor for drug screening.

To overcome the shortcomings, the present invention provides a cell and medicament dispensing device for drug screening and method thereof to mitigate or obviate the aforementioned problems.

SUMMARY OF THE INVENTION

The main objective of the present invention is to provide a cell and medicament dispensing device for drug screening and method thereof to automate the complex process of drug screening.

The cell and medicament dispensing device for drug screening is configured to inject multiple solutions into multiple solution recesses of a transfer plate. Then, liquid inside each of the solution recesses is dispensed into multiple wells of a cell culture plate with a pipette. At least one pipette-tip is detachably connected to a bottom of the pipette. The cell and medicament dispensing device comprises a base, a transfer plate serving mechanism, a transfer plate positioning mechanism, an injection mechanism, a cell culture plate positioning mechanism, and a dispensing mechanism. The base has a transfer plate entrance area, a receiving area, and a dispensing area thereon. The transfer plate serving mechanism is mounted on the base and is adjacent to the transfer plate entrance area. The transfer plate serving mechanism is configured to accommodate the transfer plate and is capable of moving the transfer plate to the transfer plate entrance area of the base. The transfer plate positioning mechanism is mounted on the base and is adjacent to the transfer plate serving mechanism. The transfer plate positioning mechanism has a positioning slider configured to connect with the transfer plate. The positioning slider is movably mounted on the base and selectively corresponds in position to the transfer plate entrance area, the receiving area, or the dispensing area. The transfer plate positioning mechanism has a sliding plate-cover which is movably mounted on the positioning slider and is movable to a position above the positioning slider to cover openings of the solution recesses of the transfer plate. The injection mechanism is mounted on the base and is adjacent to the transfer plate positioning mechanism. The injection mechanism has multiple injection heads. Each of the injection heads is in fluid communication with a respective one of the solutions and is capable of moving to the receiving area of the base. When one of the injection heads is moved into the receiving area of the base, the positioning slider is configured to align any one of the solution recesses of the transfer plate to said injection head located in the receiving area such that said injection head injects one of the solutions into the corresponding solution recess. The cell culture plate positioning mechanism is mounted on the base and configured to connect with the cell culture plate. The cell culture plate positioning mechanism has a positioning seat and a primary positioning module. The positioning seat is mounted on the base and configured to accommodate the cell culture plate. The primary positioning module is mounted on the positioning seat and configured to clamp the cell culture plate. The dispensing mechanism is mounted on the base and has a dispensing seat. The dispensing seat is configured to fix the pipette and control aspirate operation and discharge operation of the pipette. The dispensing seat is movable relative to the base and capable of moving back and forth between a position above the dispensing area of the base and a position above the cell culture plate positioning mechanism. When the dispensing seat is above the dispensing area, the dispensing seat is configured to insert the at least one pipette-tip of the pipette into any one of the solution recesses of the transfer plate and executes aspirate operation of the pipette. When the dispensing seat is above the cell culture plate positioning mechanism, the dispensing seat executes discharge operation of the pipette to release the solution liquid aspired in the pipette into one of the wells of the cell culture plate.

The cell and medicament dispensing method for drug screening comprises steps as follows:
(a) Transfer of cells or solutions: A plate feeder of a transfer plate serving mechanism moves a transfer plate to a transfer plate entrance area on a base. The transfer plate has multiple solution recesses formed thereon. A positioning slider of a transfer plate positioning mechanism moves to the transfer plate entrance area and connects with the transfer plate located in the transfer plate entrance area. The positioning slider moves the transfer plate to a receiving area on the base. An injection mechanism injects multiple solutions into the solution recesses of the transfer plate.
(b) Dispensing of cells or solutions: The positioning slider moves the transfer plate to a dispensing area on the base. A cell culture plate with multiple wells is ready at a position by the cell culture plate positioning mechanism. A dispensing mechanism moves a pipette back and forth between a position above the dispensing area on the base and a position above the cell culture plate on the positioning slider to dispense liquid in each of the solution recesses into the wells of the cell culture plate.

The advantage of the present invention is that liquids and cells for drug screening are automatically transferred to the solution recesses of the transfer plate by coordination among the transfer plate serving mechanism, the transfer plate positioning mechanism, and the injection mechanism. Afterwards, the liquid in each of the solution recesses is automatically dispensed into the wells of the cell culture plate by coordination between the transfer plate positioning mechanism and the dispensing mechanism. As a result, the process of drug screening could be automated to reduce labor and improve quality.

Other objectives, advantages and novel features of the invention will become more apparent from the following detailed description when taken in conjunction with the accompanying drawings.

DETAILED DESCRIPTION OF THE PREFERRED EMBODIMENTS

Figure 24:
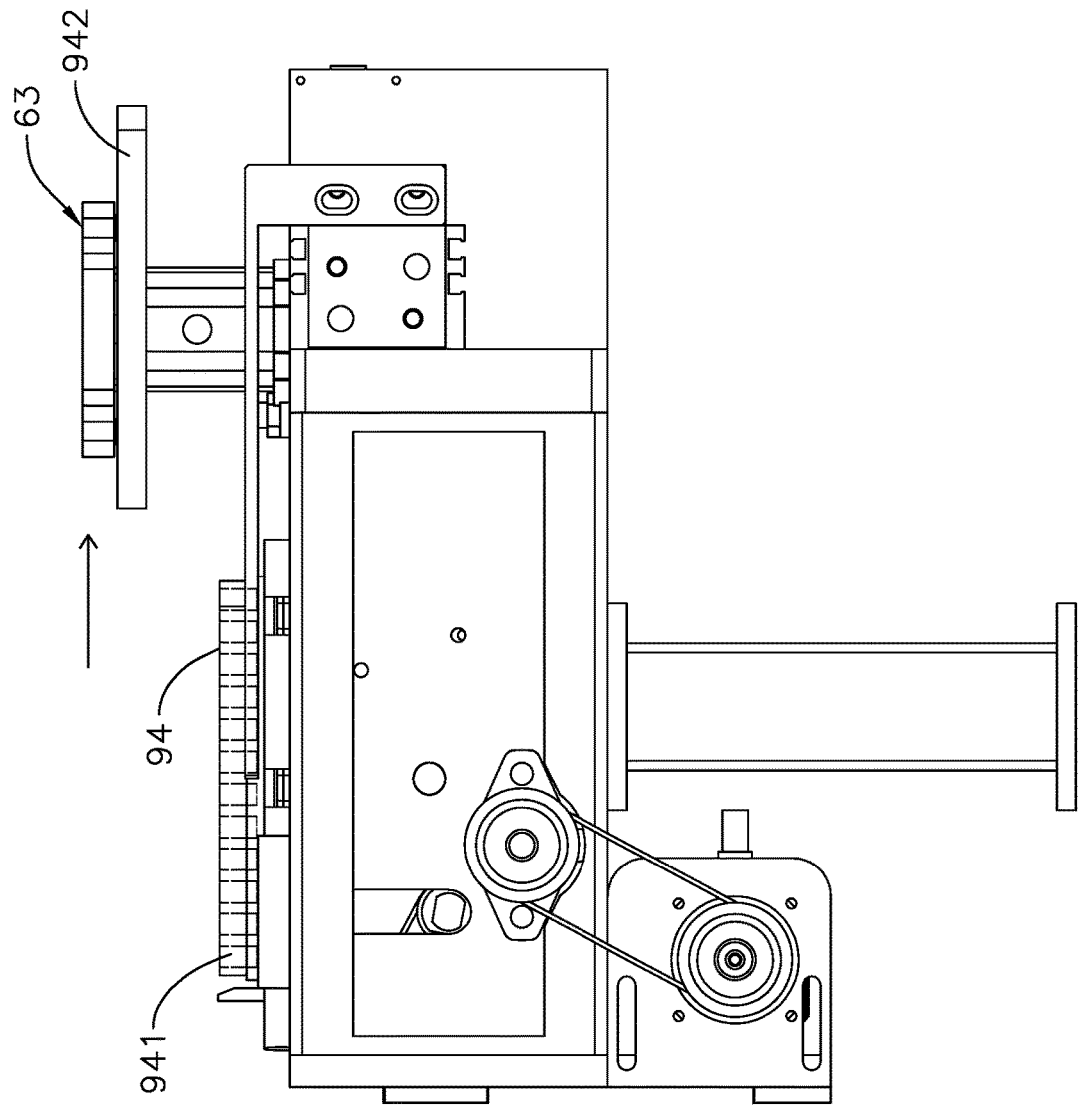
Figure 25:
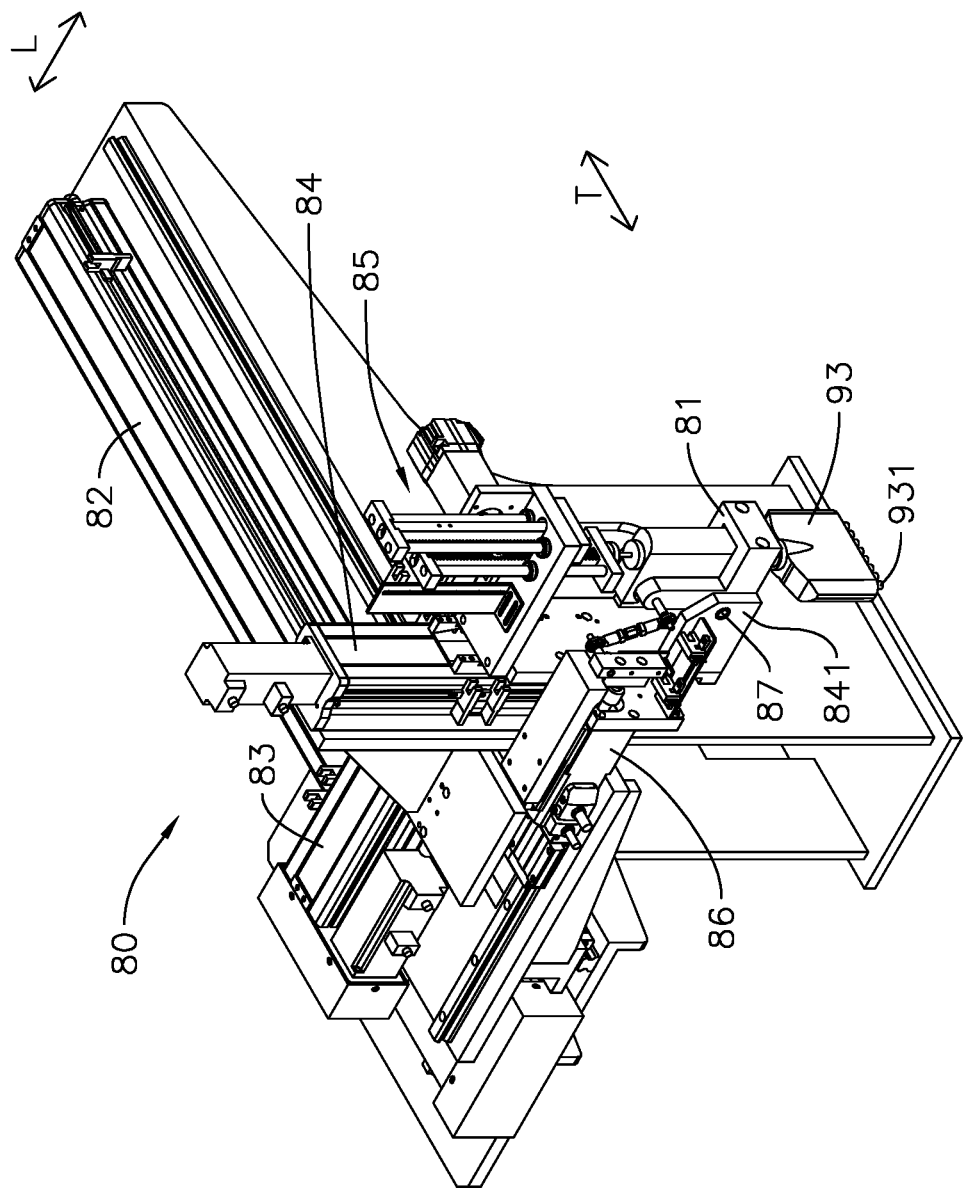
FIG. 25 is a perspective view of a dispensing mechanism of the cell and medicament dispensing device in FIG. 1.
Figure 32:
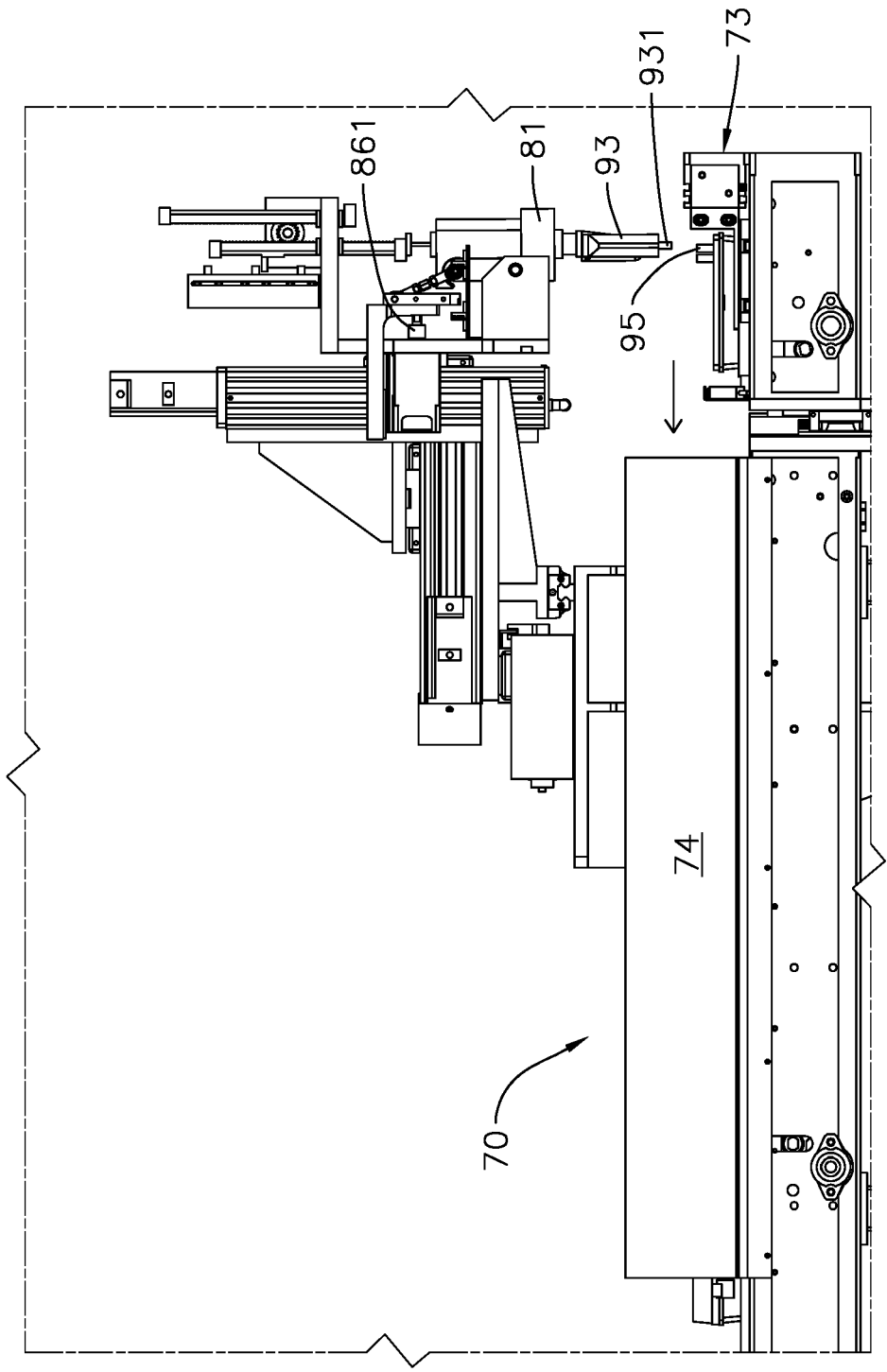

With reference to FIGS. 2, 3, 6, 24, 25, and 27, a cell and medicament dispensing device for drug screening in accordance with the present invention is configured to inject multiple solutions 91 into multiple solution recesses 921 of a transfer plate 92, and then liquid inside each of the solution recesses 921 is dispensed into multiple wells 941 (as shown in FIG. 24) of a cell culture plate 94 with a pipette 93. Each of the solutions 91 comprises one single type of medicament or one single type of cells. At least one cylindrical pipette-tip 95 (as shown in FIG. 32) is detachably connected to a tip connector 931 (as shown in FIG. 25) at bottom of the pipette 93. The cell culture plate 94 preferably has an upper lid 942 detachably covering the wells 941.

Figure 2:
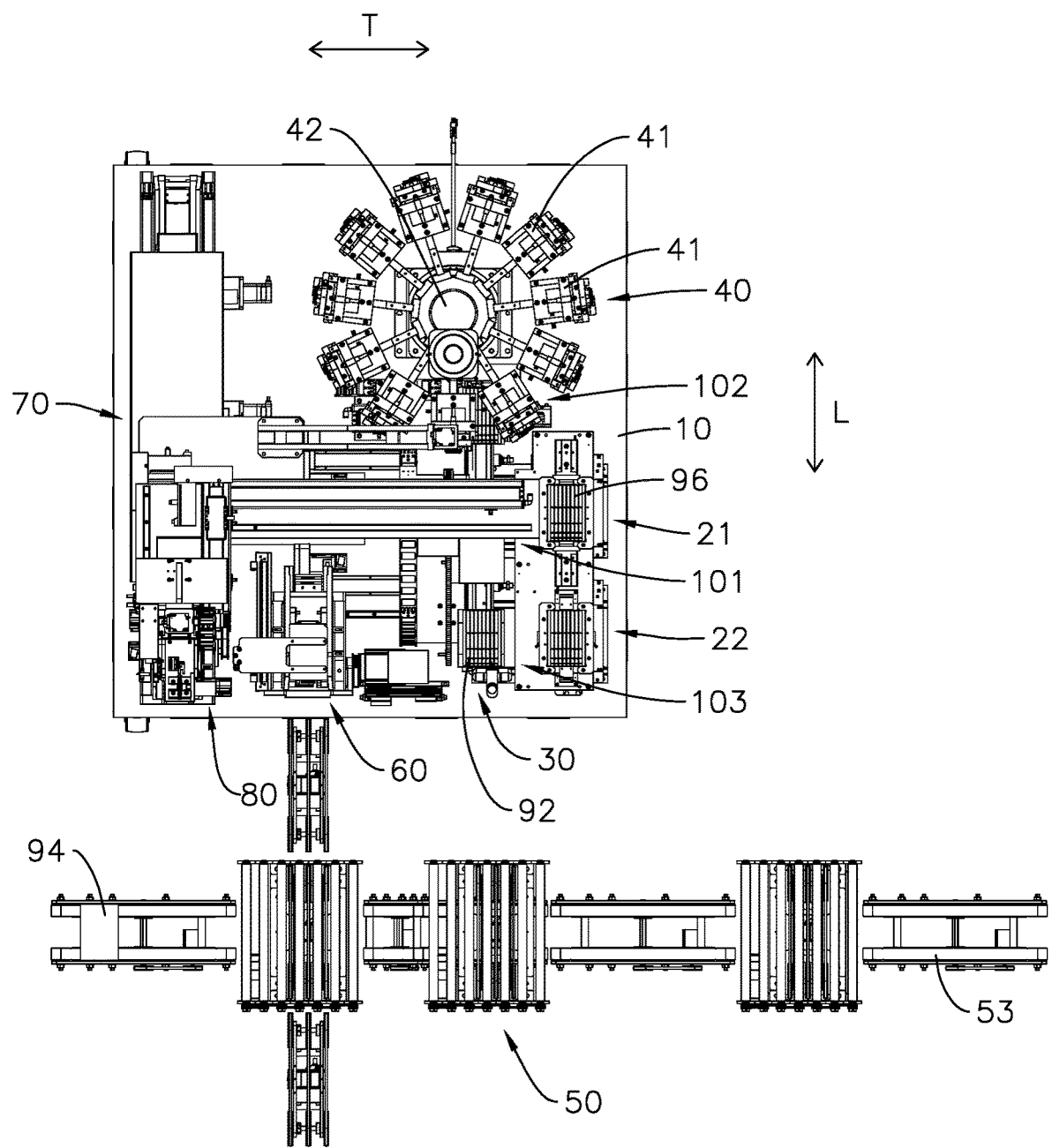
FIG. 2 is a schematic top view of the cell and medicament dispensing device in FIG. 1.
Figure 3:
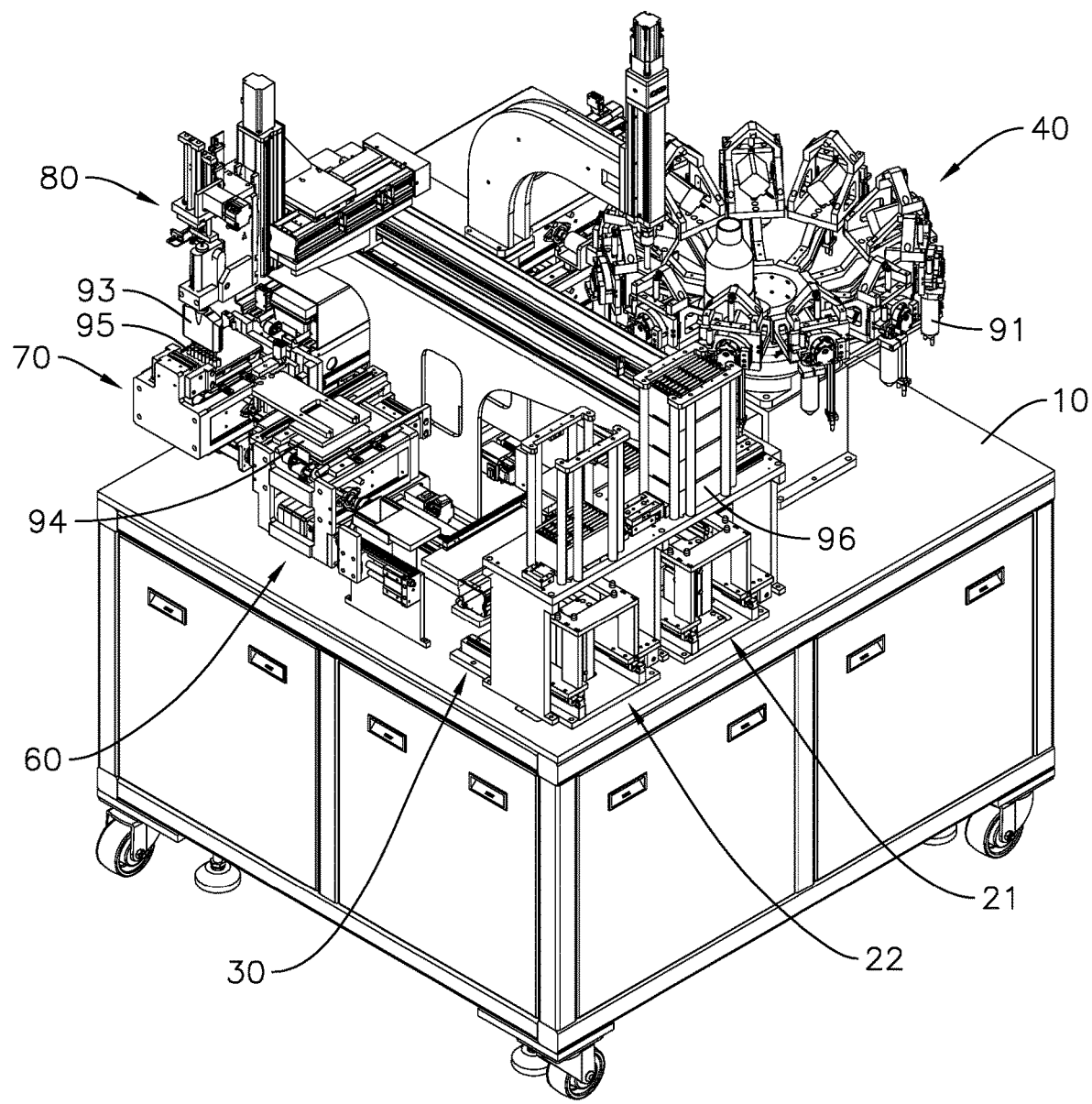
FIG. 3 is a partial perspective view of the cell and medicament dispensing device in FIG. 1.
Figure 4:
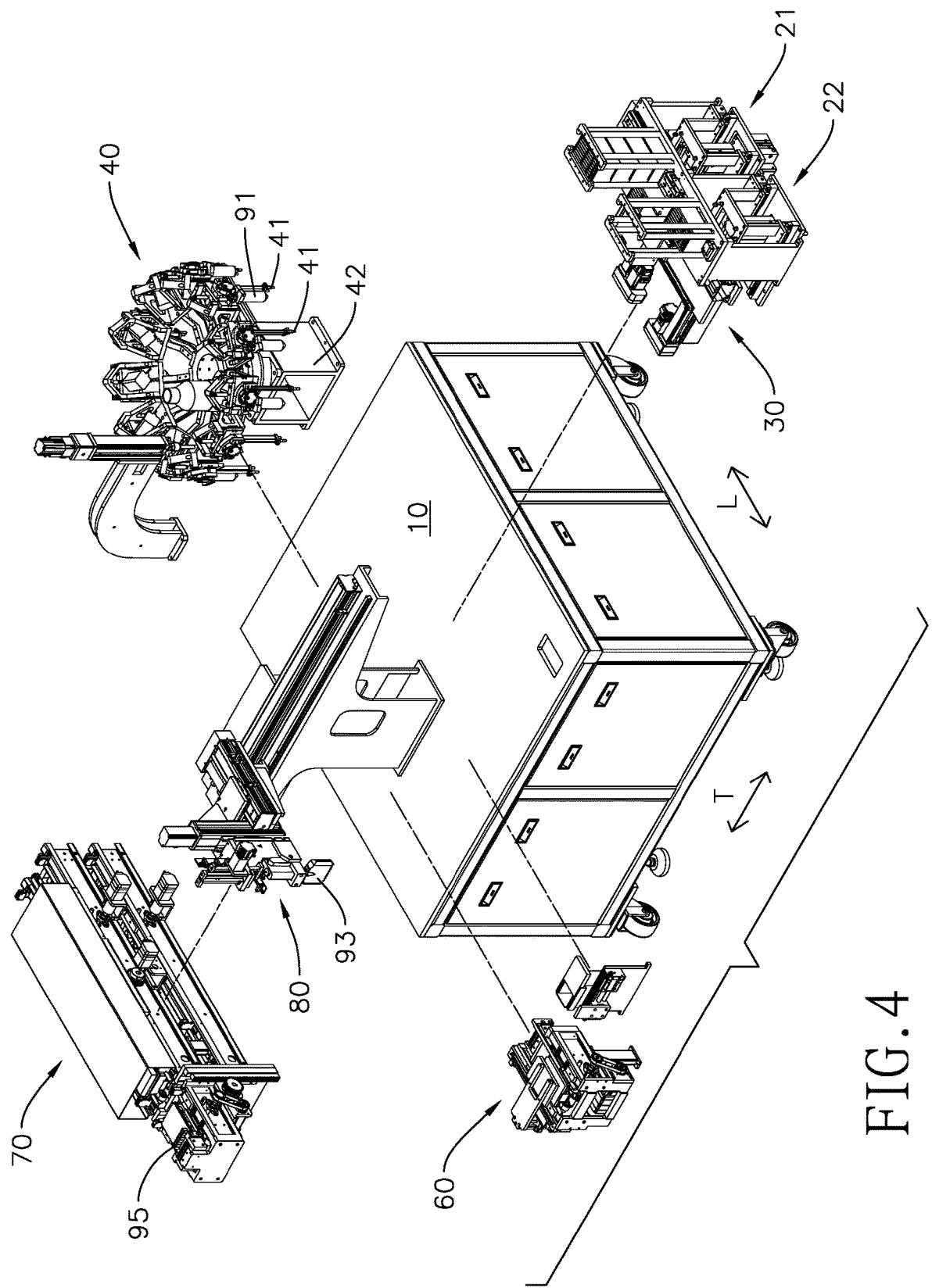
FIG. 4 is an exploded view of the cell and medicament dispensing device in FIG. 3.

With reference to FIGS. 2 to 4, the cell and medicament dispensing device has a base 10, a transfer plate serving mechanism 21, a transfer plate positioning mechanism 30, an injection mechanism 40, a cell culture plate positioning mechanism 60, and a dispensing mechanism 80. In the present embodiment, the cell and medicament dispensing device further has a cell culture plate conveyer 50, a pipette-tip feeder 70, and a transfer plate retriever 22.

The base 10 has a transfer plate entrance area 101, a receiving area 102, and a dispensing area 103 disposed thereon. The transfer plate entrance area 101, the receiving area 102, and the dispensing area 103 are disposed apart from each other along a longitudinal direction L of the base 10.

Figure 5:
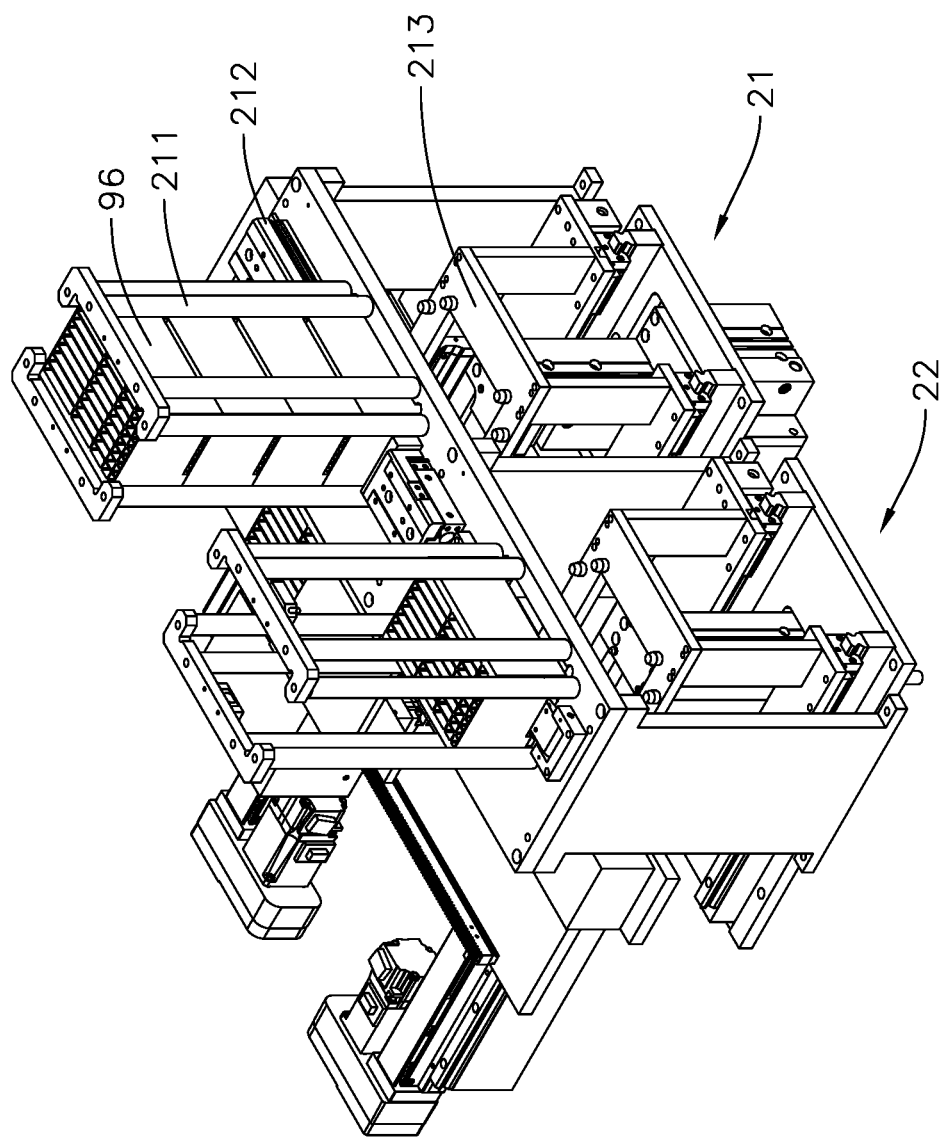
FIG. 5 is a partial perspective view of the cell and medicament dispensing device in FIG. 1, showing a transfer plate serving mechanism, a transfer plate retriever, and a transfer plate positioning mechanism of the dispensing device.
Figure 6:
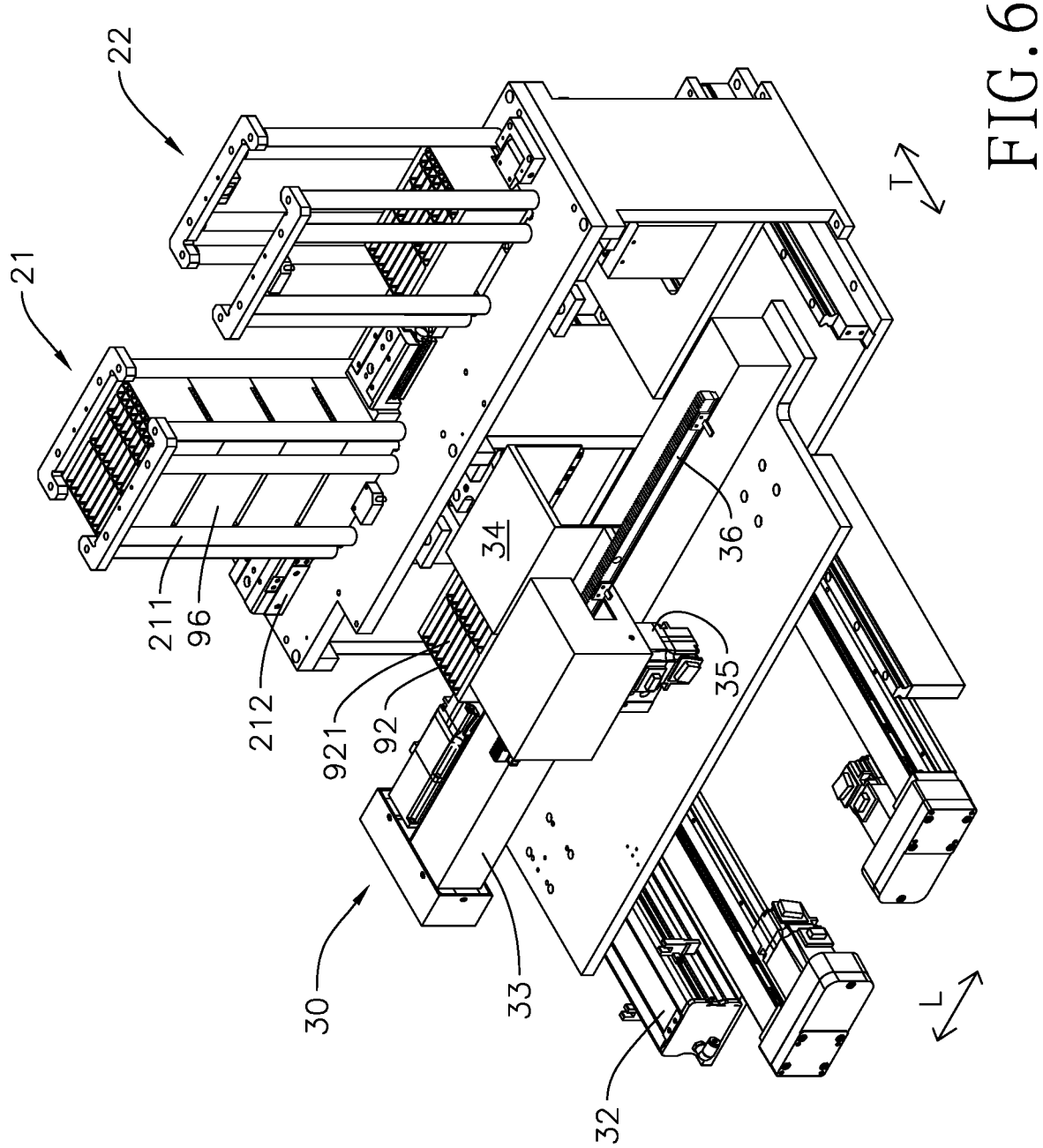
FIG. 6 is a partial perspective view of the cell and medicament dispensing device in FIG. 1, showing the transfer plate serving mechanism, the transfer plate retriever, and the transfer plate positioning mechanism from another angle.
Figure 7:
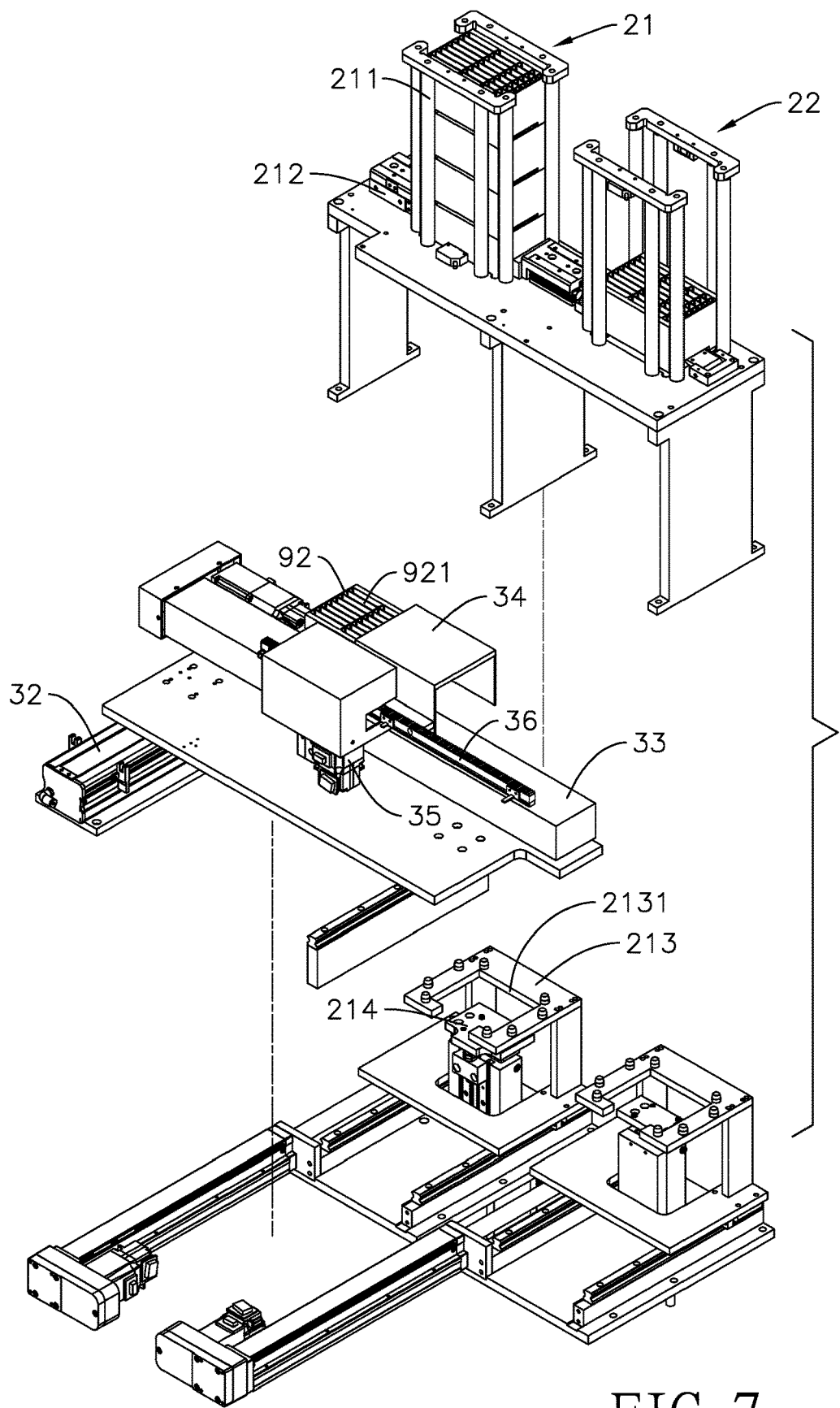
FIG. 7 is an exploded perspective view of the transfer plate serving mechanism, the transfer plate retriever, and the transfer plate positioning mechanism of the cell and medicament dispensing device in FIG. 6.

With reference to FIGS. 5 to 7, the transfer plate serving mechanism 21 is mounted on the base 10 and is adjacent to the transfer plate entrance area 101. A transfer plate 92 is accommodated in the transfer plate serving mechanism 21, and the transfer plate serving mechanism 21 is capable of moving the transfer plate 92 to the transfer plate entrance area 101 of the base 10. In the preferred embodiment, the transfer plate serving mechanism 21 has a plate stacking bracket 211, two plate-locking clamps 212, a plate feeder 213, and a plate lifting actuator 214.

Figure 8:
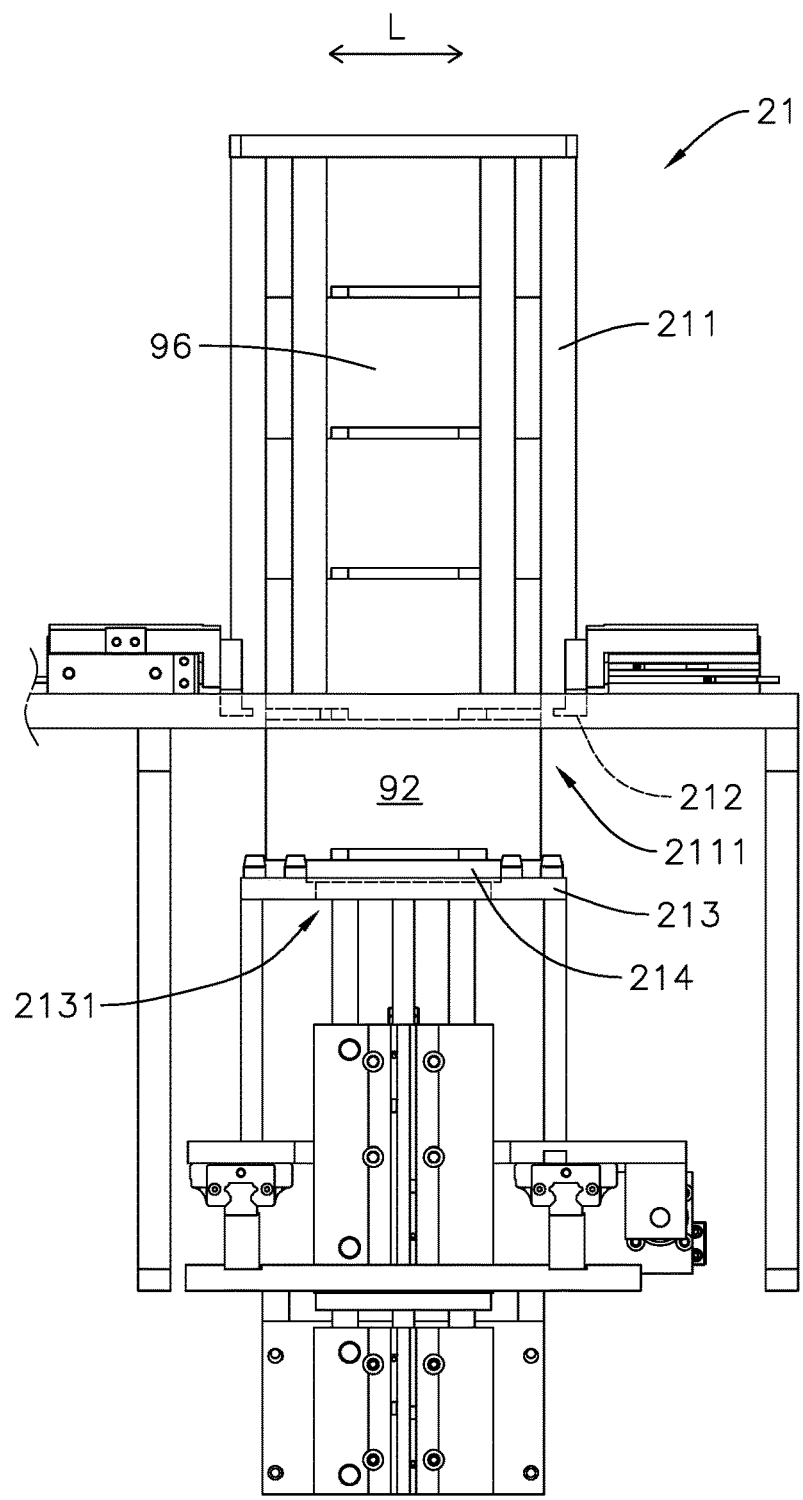
FIG. 8 and FIG. 9 are operational schematic side views of the cell and medicament dispensing device in FIG. 1, showing operating statuses of the transfer plate serving mechanism viewed along a transverse direction.
Figure 9:
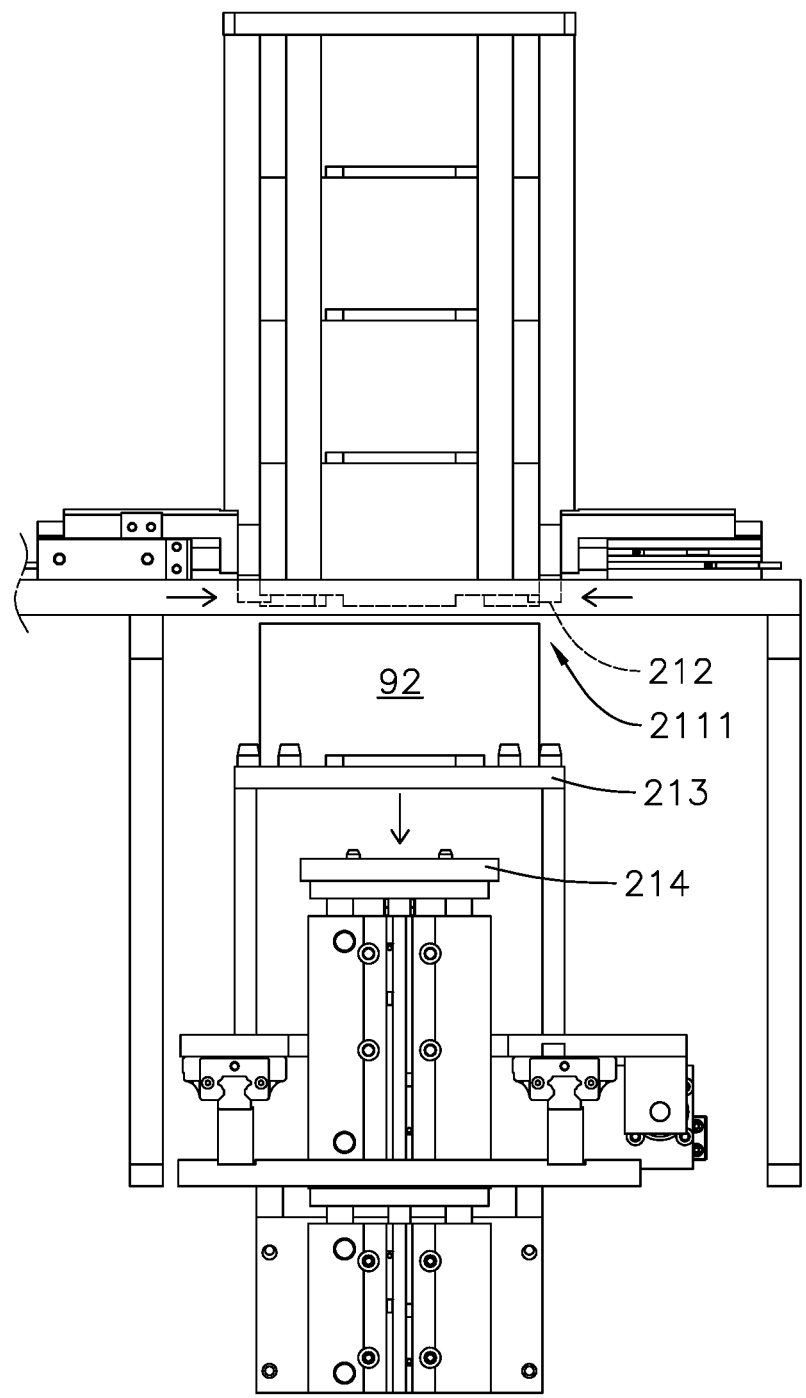

With reference to FIGS. 8 and 9, the plate stacking bracket 211 forms a stacking space. The stacking space is configured to accommodate multiple spare transfer plates 96 that are stacked vertically. A plate dropping opening 2111 is formed in a bottom of the plate stacking bracket 211. The spare transfer plates 96 in the stacking space are capable of dropping down through the plate dropping opening 2111.

Each of the two plate-locking clamps 212 is mounted on a respective side of two opposite sides of the plate dropping opening 2111. The two plate-locking clamps 212 are capable of moving toward each other to prevent the spare transfer plates 96 from passing through the plate dropping opening 2111.

The plate feeder 213 is mounted under the plate dropping opening 2111 and is configured to receive the transfer plate 92 or the spare transfer plates 96 dropping down from the plate dropping opening 2111. With reference to FIGS. and 11, the plate feeder 213 is capable of moving to the transfer plate entrance area 101 on the base 10. With reference to FIGS. 8 and 9, the plate feeder 213 has a plate lifting opening 2131 which is formed through two opposite sides of the plate feeder 213. With reference to FIGS. 7 and 8, the plate lifting actuator 214 is mounted under the plate lifting opening 2131 and capable of moving upward to protrude through the plate lifting opening 2131.

The transfer plate positioning mechanism 30 is mounted on the base 10 and adjacent to the transfer plate serving mechanism 21. The transfer plate positioning mechanism 30 has a positioning slider 31, a first plate linear module 32, a second plate linear module 33, a sliding plate-cover 34, a cover driving motor 35, and a cover gear rack 36.

With reference to FIGS. 6, 7, and 14 to 16, the positioning slider 31 is configured to connect with the transfer plate 92. The positioning slider 31 is movably mounted on the base 10 and selectively corresponds in position to the transfer plate entrance area 101, the receiving area 102, or the dispensing area 103.

To be specific, the first plate linear module 32 is mounted on the base 10 and extends along a transverse direction T of the base 10. The second plate linear module 33 is mounted on the first plate linear module 32 and extends along the longitudinal direction L of the base 10. The positioning slider 31 is mounted on the second plate linear module 33 such that the positioning slider 31 is movable in both the longitudinal direction L and transverse direction T.

In the preferred embodiment, the plate feeder 213 of the transfer plate serving mechanism 21 is movable to a position above the positioning slider 31, and the positioning slider 31 is capable of moving upward and downward such that the transfer plate 92 can be transferred from the plate feeder 213 to the positioning slider 31. Detailed operating steps of the positioning slider 31 are as described below.

Figure 10:
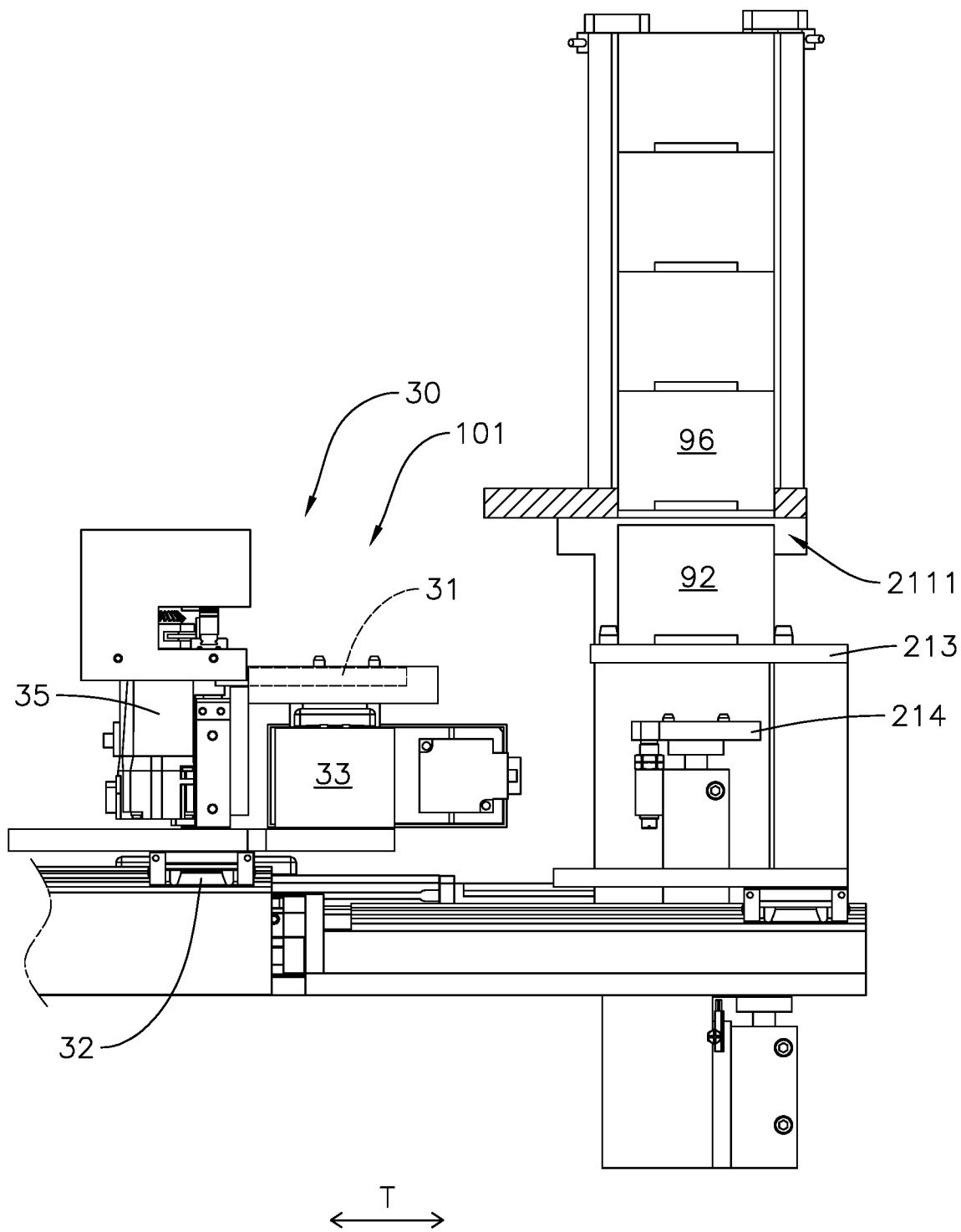
FIGS. 10 to 13 are operational schematic cross sectional views of the cell and medicament dispensing device in FIG. 1, showing operating statuses of the transfer plate serving mechanism and the transfer plate positioning mechanism viewed along a longitudinal direction.
Figure 11:
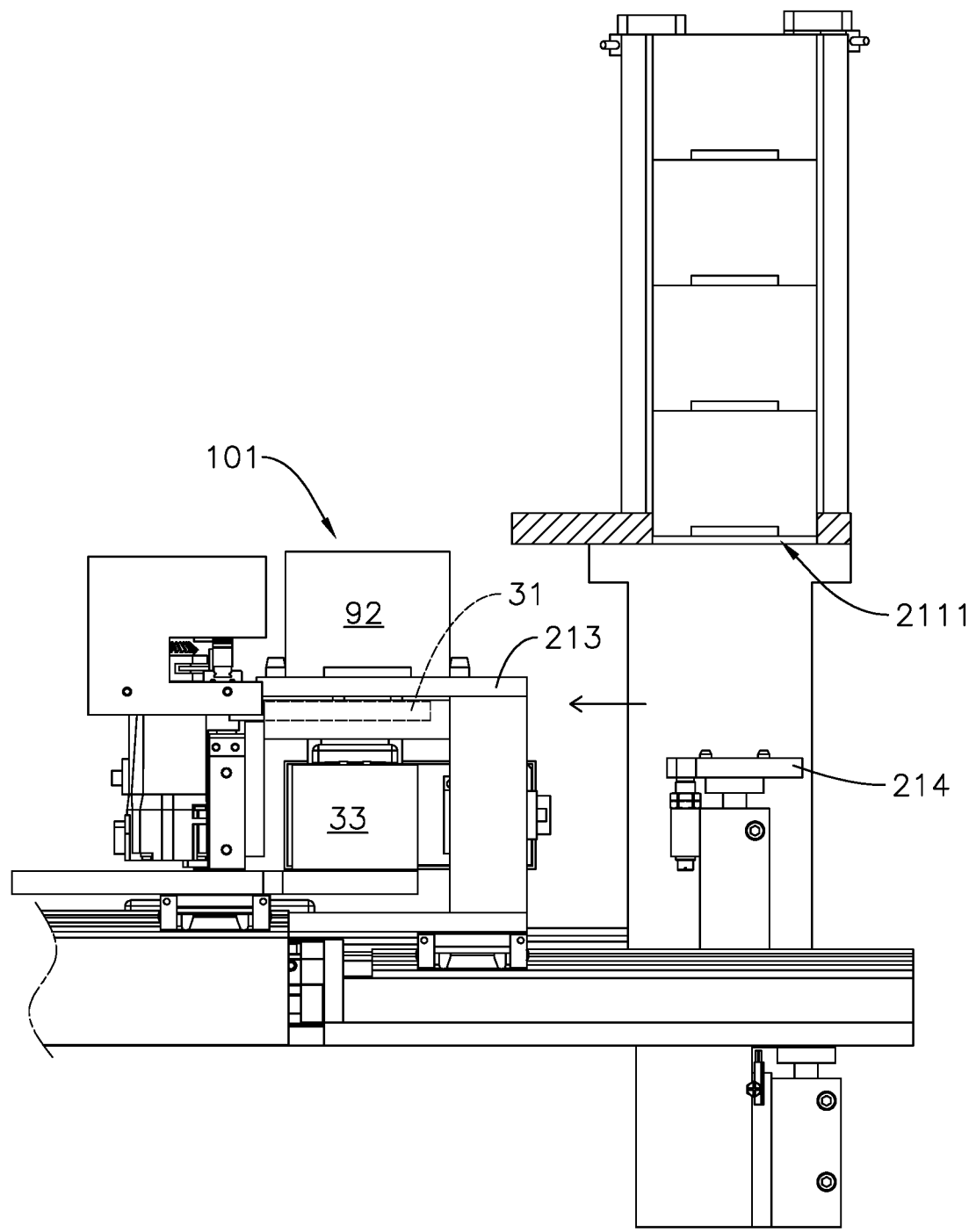

1. With reference to FIGS. 10 to 11, the positioning slider 31 moves to the transfer plate entrance area 101, and the plate feeder 213 moves to the position above the positioning slider 31.

Figure 12:
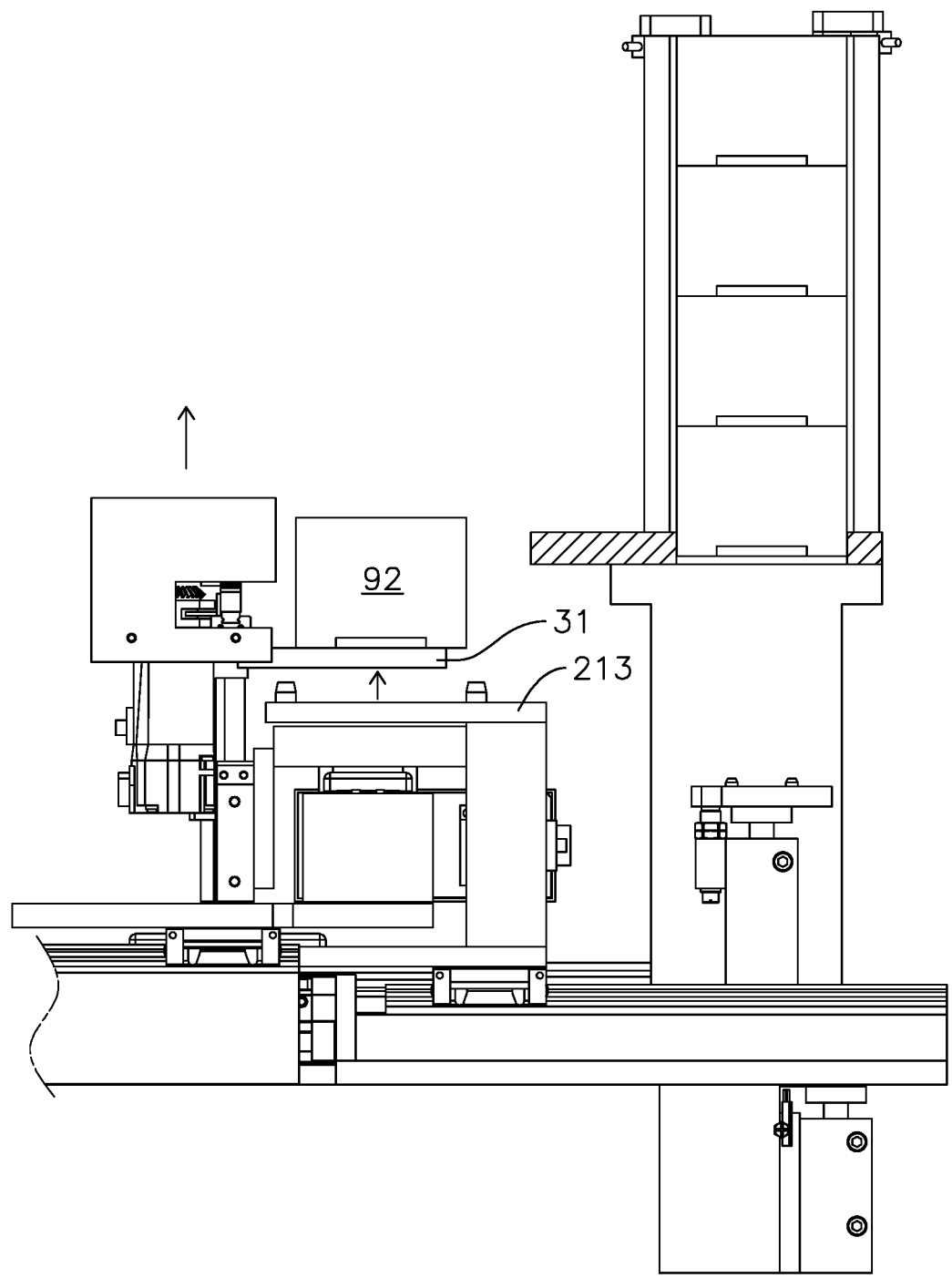

2. With reference to FIGS. 11 and 12, the positioning slider 31 moves upward to protrude through the plate feeder 213 via the plate lifting opening such that the transfer plate 92 rested on the plate feeder 213 is lifted by the positioning slider 31 and connected with the positioning slider 31.

Figure 13:
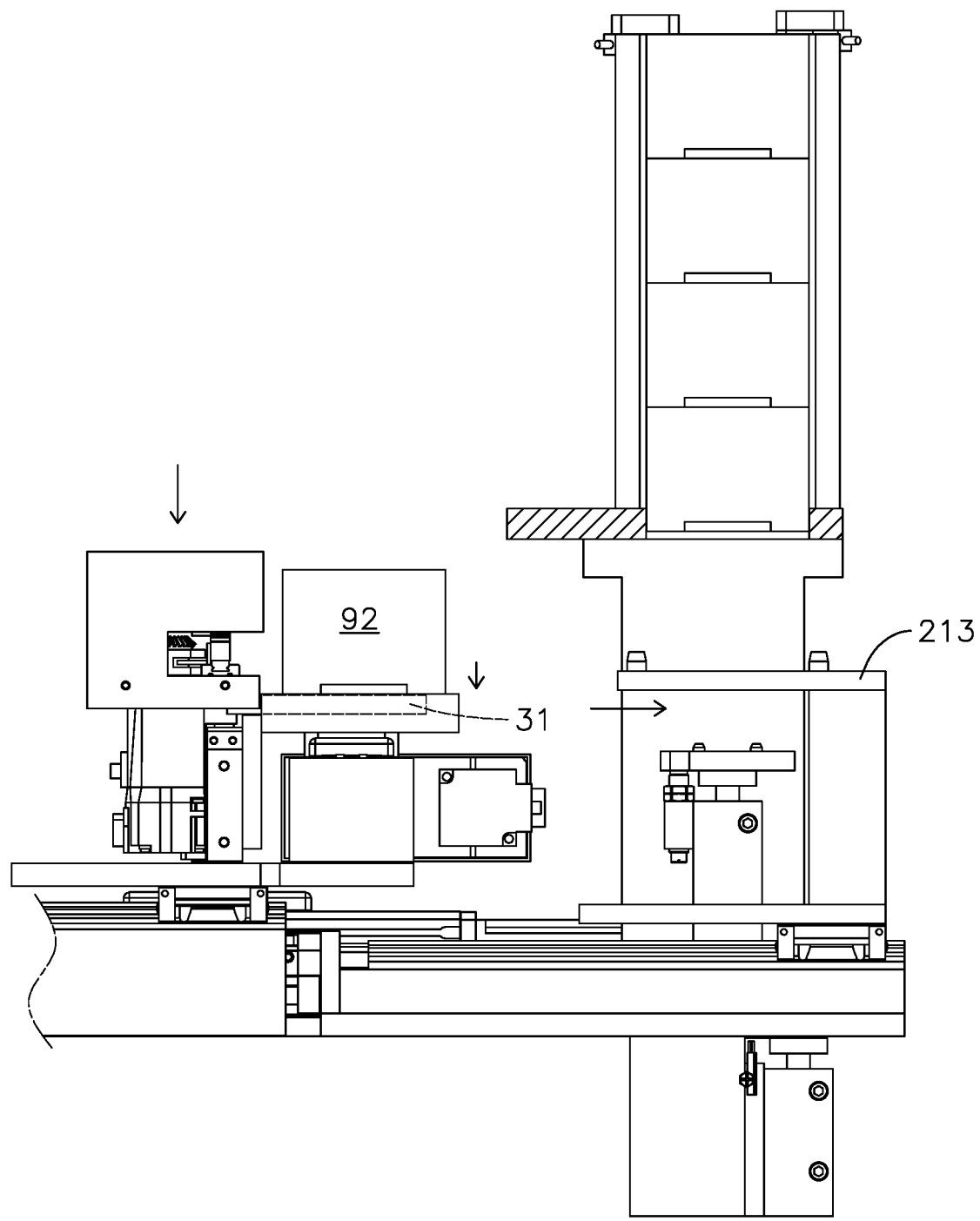

3. With reference to FIGS. 12 and 13, the plate feeder 213 moves away from the position above the positioning slider 31, and then the positioning slider 31 moves downward to return to its original height position.

Figure 15:
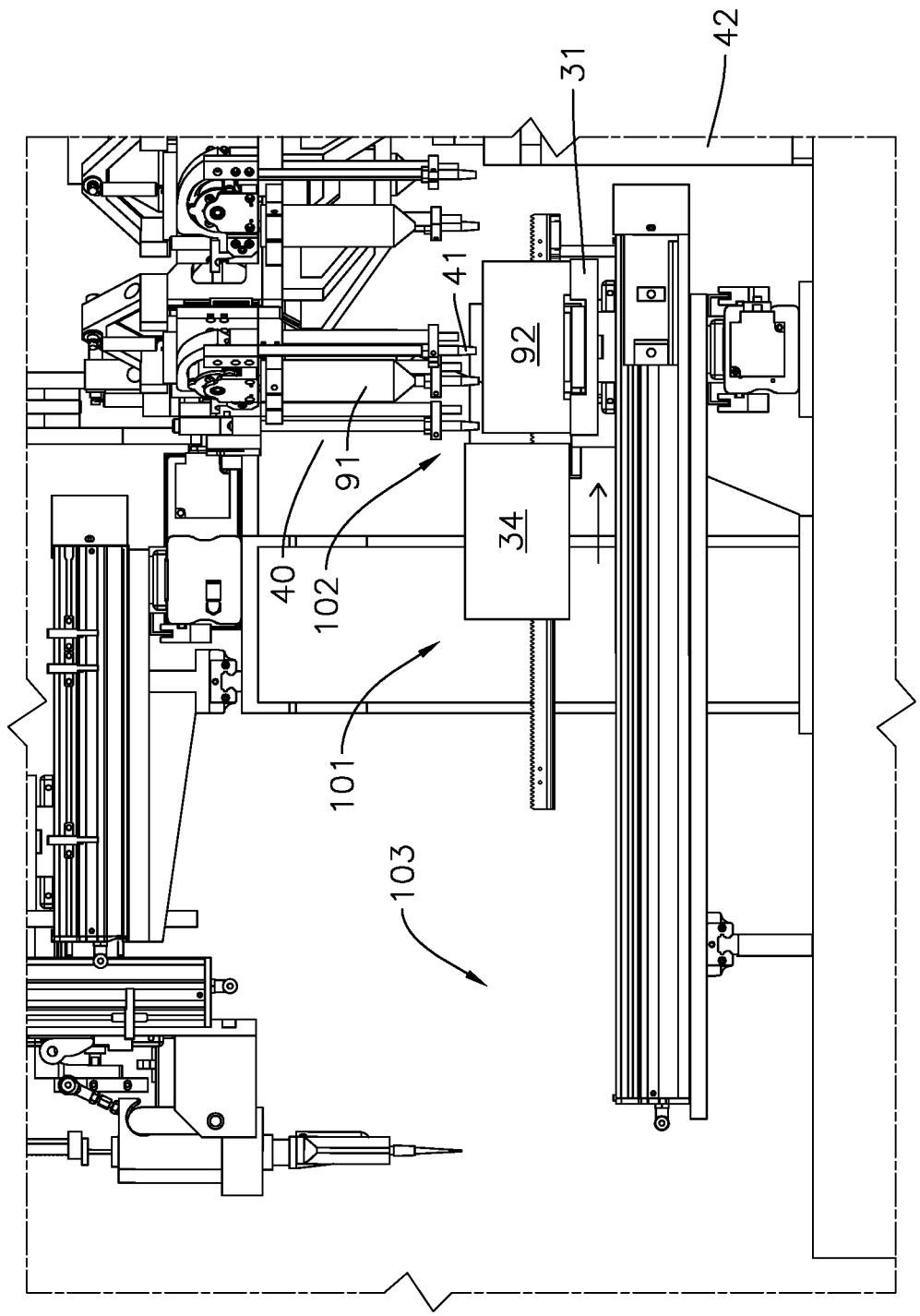
Figure 16:
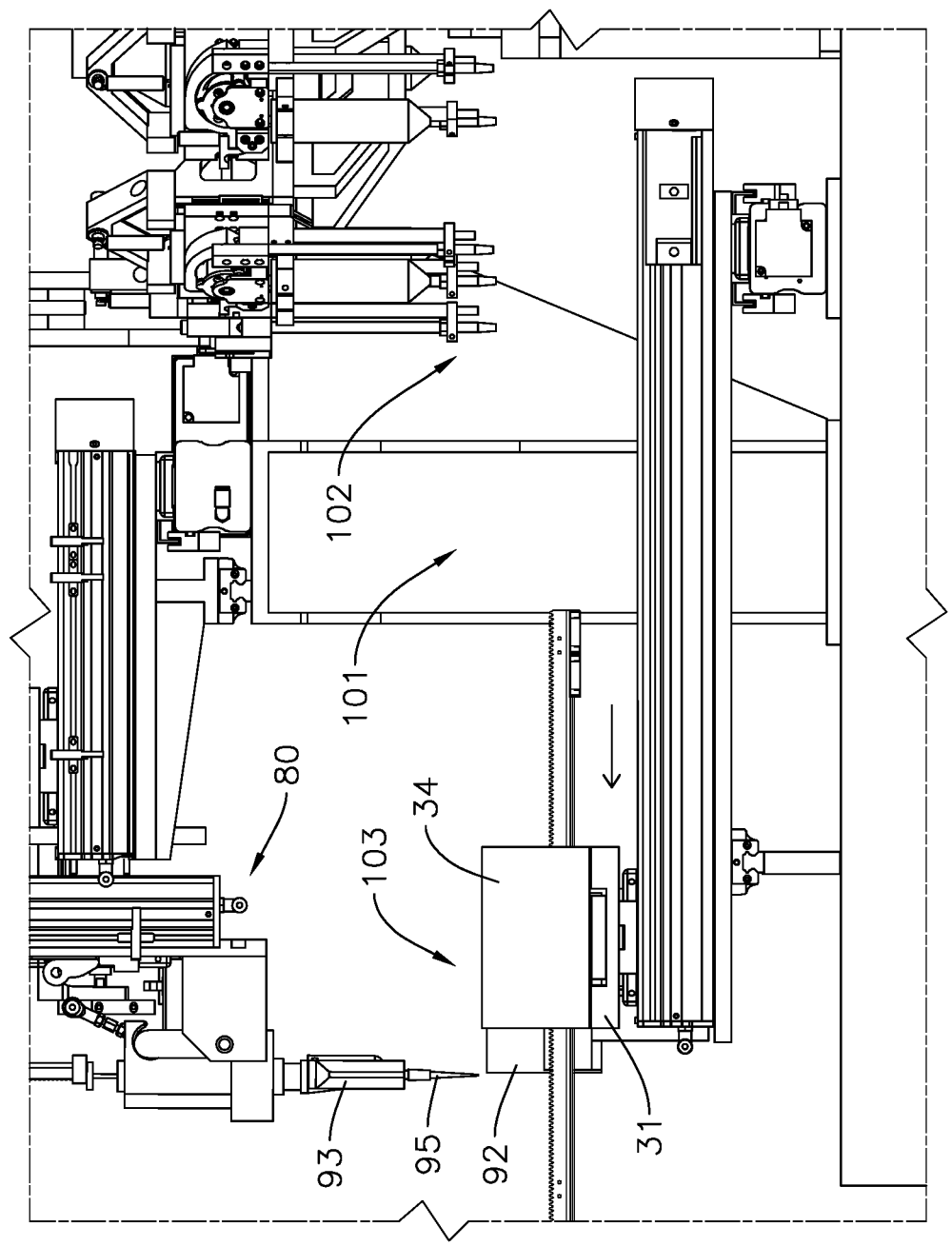

With reference to FIGS. 6, 15, and 16, the cover driving motor 35 is mounted on the positioning slider 31. The cover gear rack 36 is mounted on the positioning slider 31, is movable along the longitudinal direction L, and is coupled to an output axis of the cover driving motor 35. The sliding plate-cover 34 is fixed to the cover gear rack 36 such that when the cover gear rack 36 moves relative to the positioning slider 31, the sliding plate-cover 34 is driven by the cover gear rack 36 to move relative to the positioning slider 31. As a result, the sliding plate-cover 34 is movable to a position above the positioning slider 31 to cover the transfer plate 92 and to prevent foreign objects from falling into the solution recesses 921.

The structure for moving the sliding plate-cover 34 is not limited thereby, as long as the sliding plate-cover 34 is capable of selectively covering the solution recesses 921 of the transfer plate 92.

The injection mechanism 40 is mounted on the base 10 and adjacent to the transfer plate positioning mechanism 30. The injection mechanism 40 has multiple injection heads 41. Each of the injection heads 41 is in fluid communication with a respective one of the solutions 91, and is movable to the receiving area 102 of the base 10. The aforementioned positioning slider 31 is configured to align any one of the solution recesses 921 of the transfer plate 92 to the injection head 41 that is located in the receiving area 102 such that said injection head 41 injects one of the solutions 91 into the corresponding solution recess 921.

In the preferred embodiment, the injection mechanism 40 has a rotary seat 42 rotatably mounted on the base 10. The injection heads 41 are mounted on the rotary seat 42 and disposed apart from each other around a rotating axis of the rotary seat 42. Rotation of the rotary seat 42 moves the injection heads 41 to the receiving area 102 for a given positioning, and then the injection head 41 in the receiving area 102 is aligned to the respective solution recess 921 by controlling the positioning slider 31 to the fine-tune position of the transfer plate 92 in both the longitudinal direction L and the transverse direction T.

Figure 1:
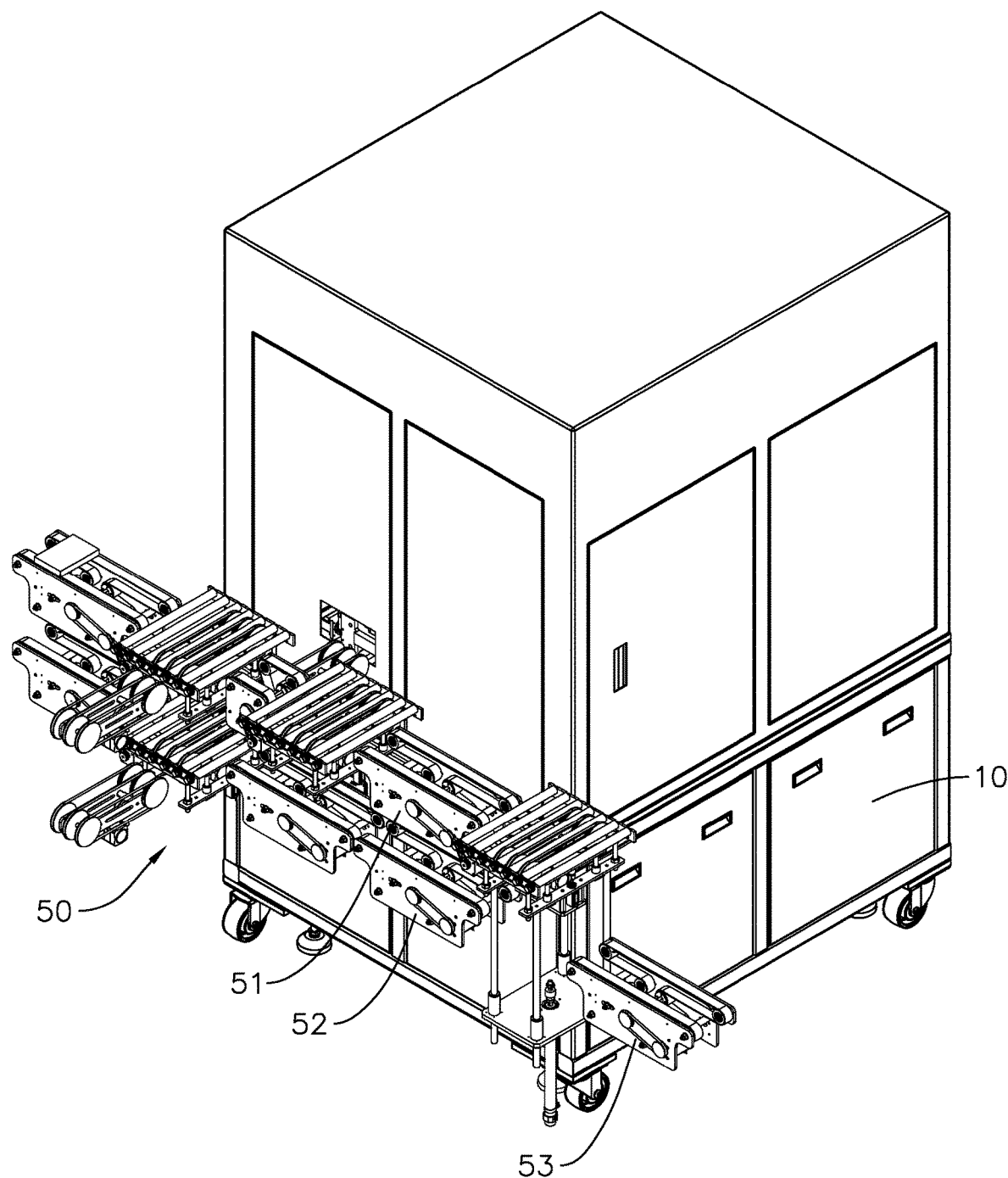
FIG. 1 is a perspective view of a cell and medicament dispensing device for drug screening in accordance with the present invention.

With reference to FIGS. 1 and 2, the cell culture plate conveyer 50 is located on a side of the base 10 and configured to deliver the ready-to-process cell culture plate 94 from a cell culture device (not shown in figures) to the base 10. Processed cell culture plate 94 is also returned to the cell culture device by the cell culture plate conveyer 50.

The cell culture plate conveyer 50 has an input conveyor belt 51, an output conveyor belt 52, and a cell culture plate elevator 53. The input conveyor belt 51 is configured to deliver the ready-to-process cell culture plate 94 to the cell culture plate positioning mechanism 60. The output conveyor belt 52 is disposed under the input conveyor belt 51. The input conveyor belt 51 and the output conveyor belt 52 operate in reverse directions. The cell culture plate elevator 53 is mounted to an end of the input conveyor belt 51, and is capable of moving downward to an end of the output conveyor belt 52 to transfer the cell culture plate 94 from the input conveyor belt 51 to the output conveyor belt 52.

Figure 17:
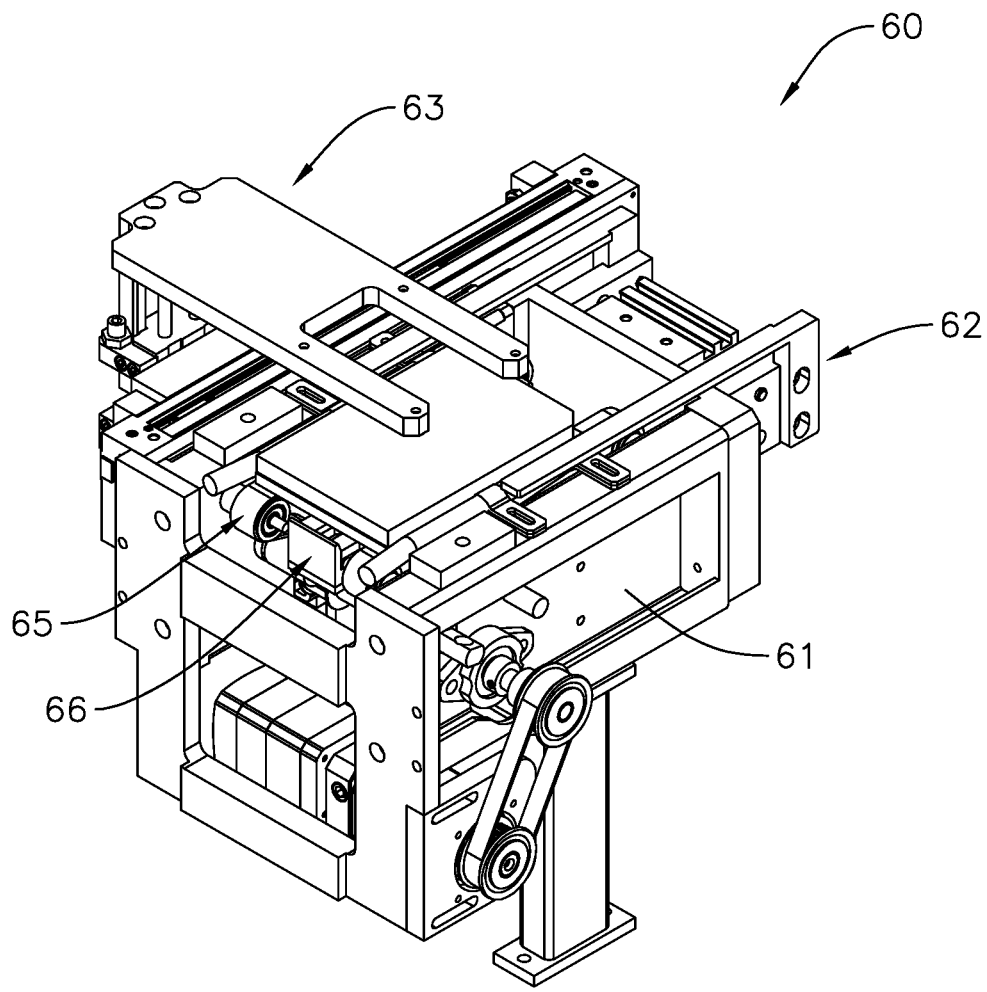
FIG. 17 is a perspective view of a cell culture plate positioning mechanism of the cell and medicament dispensing device in FIG. 1.
Figure 18:
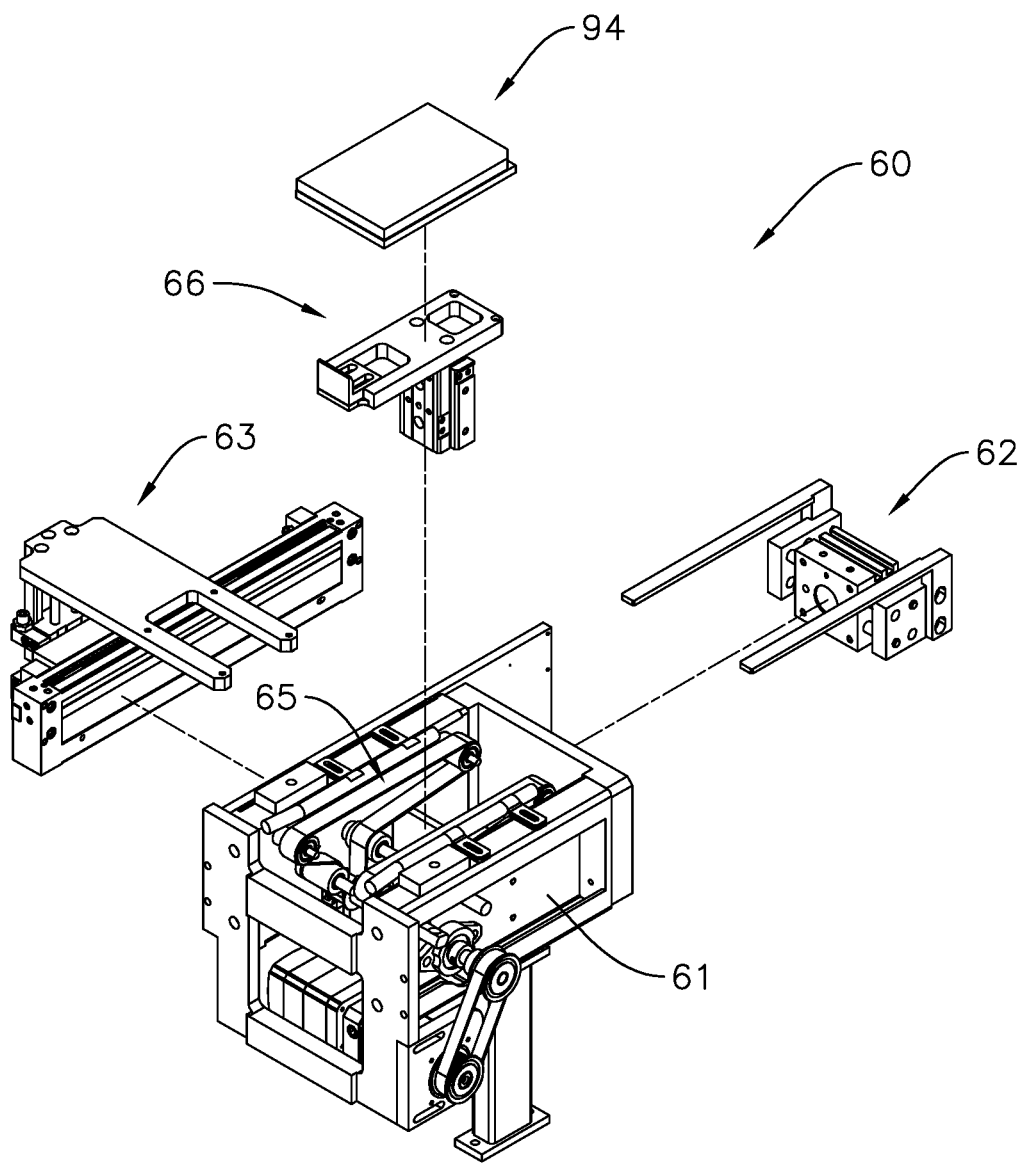
FIG. 18 is an exploded perspective view of the cell culture plate positioning mechanism of the cell and medicament dispensing device in FIG. 17.

With reference to FIGS. 17 and 18, the cell culture plate positioning mechanism 60 is mounted on the base 10 and configured to connect with the cell culture plate 94. The cell culture plate positioning mechanism 60 has a positioning seat 61 and a primary positioning module 62; in the preferred embodiment, the cell culture plate positioning mechanism 60 further has a lid opener 63, multiple suction cups 64, a cell culture plate transfer module 65, and a secondary positioning module 66.

The positioning seat 61 is mounted on the base 10 and configured to accommodate the cell culture plate 94. In the preferred embodiment, the cell culture plate 94 is automatically delivered to the positioning seat 61 by the cell culture plate conveyer 50. Processed cell culture plates 94 are also returned to the cell culture device by the cell culture plate conveyer 50.

Figure 21:
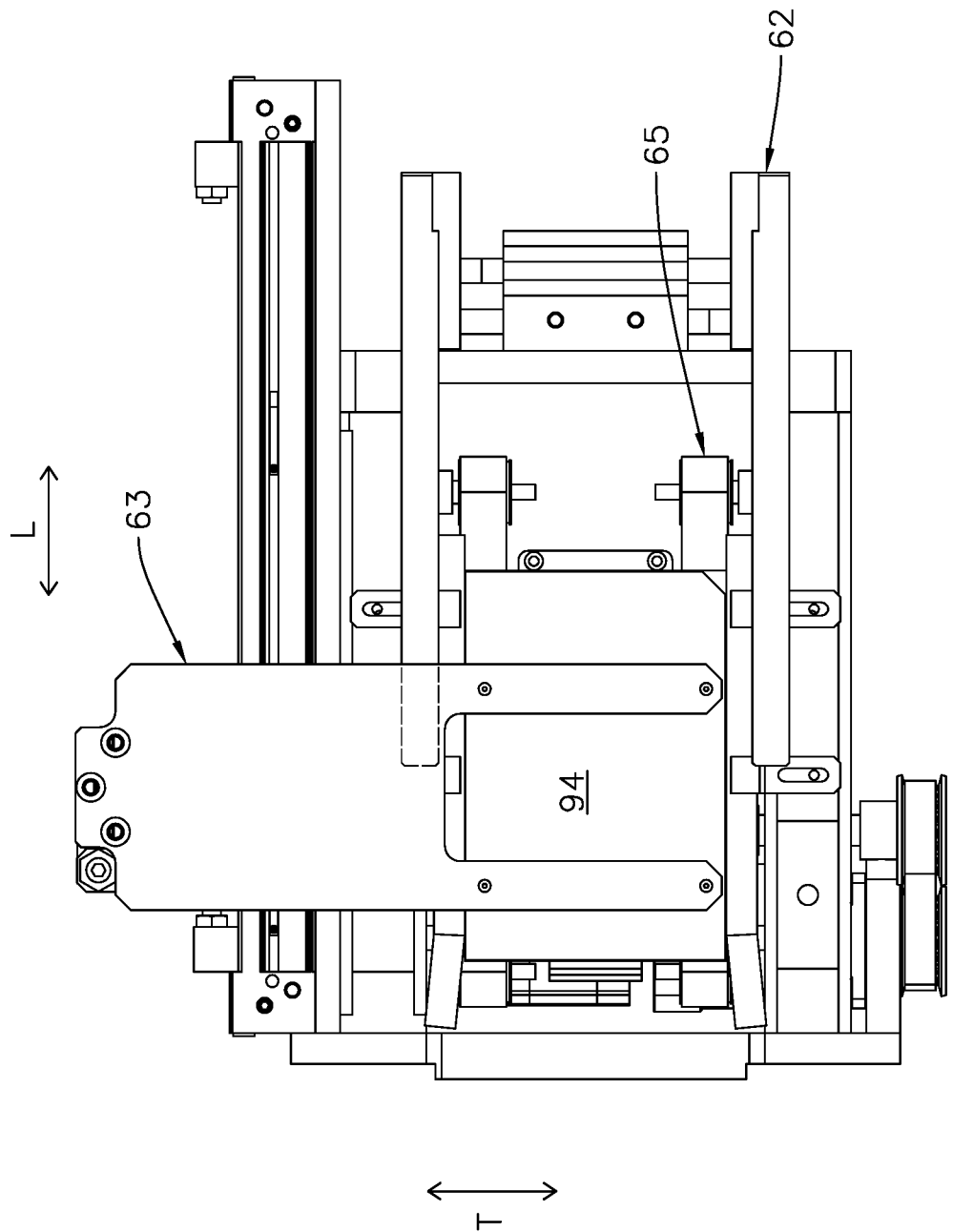
FIGS. 21 and 22 are operational schematic top views of the cell culture plate positioning mechanism of the cell and medicament dispensing device in FIG. 17, showing operating statuses of the cell culture plate positioning mechanism.
Figure 22:
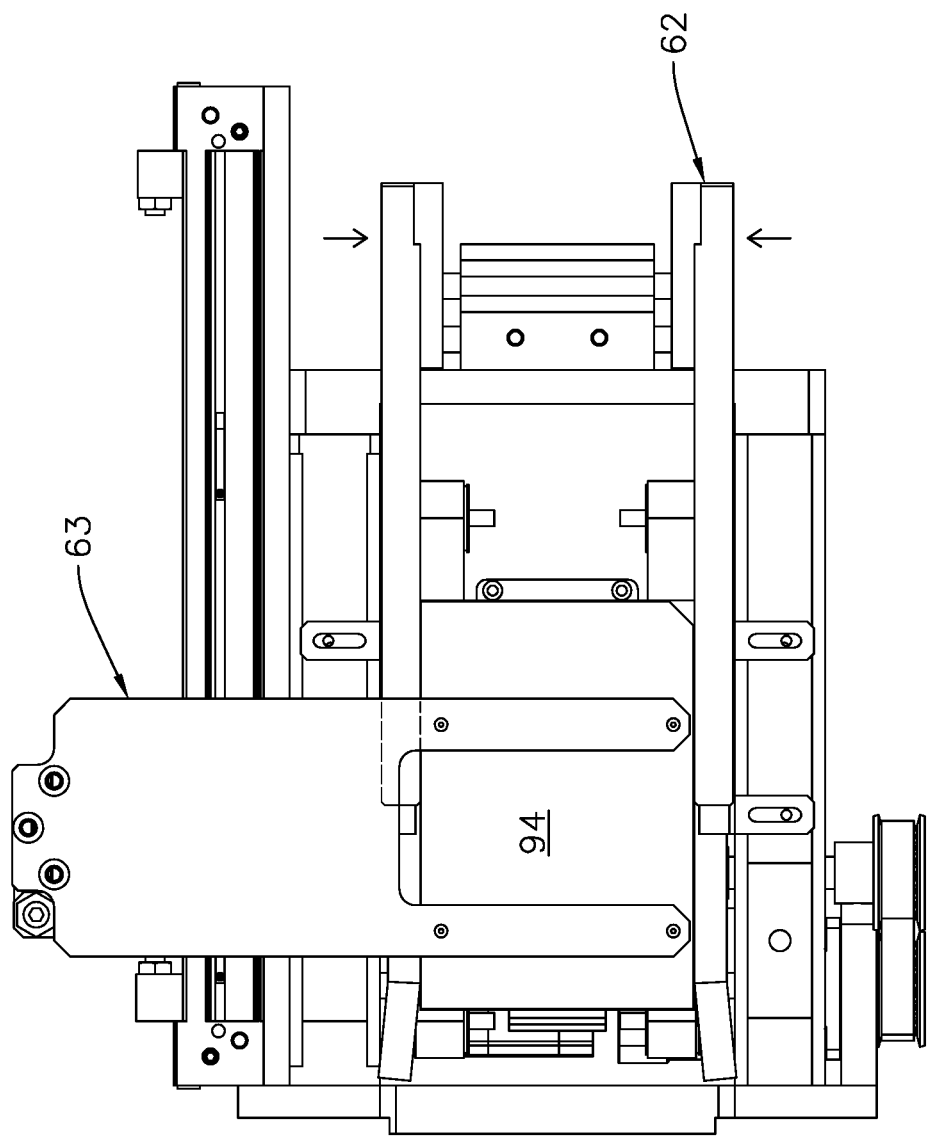

With reference to FIGS. 21 and 22, the primary positioning module 62 is mounted on the positioning seat 61 and configured to clamp the two opposite sides of the cell culture plate 94. To be precise, the primary positioning module 62 is a 2-Jaw parallel gripper, and can be controlled to clamp the cell culture plate 94 such that a position of the cell culture plate 94 in the transverse direction T is fixed. The primary positioning module 62 preferably clamps the two opposite sides of the cell culture plate 94 that face toward and move longitudinally away from the transverse direction T.

Figure 23:
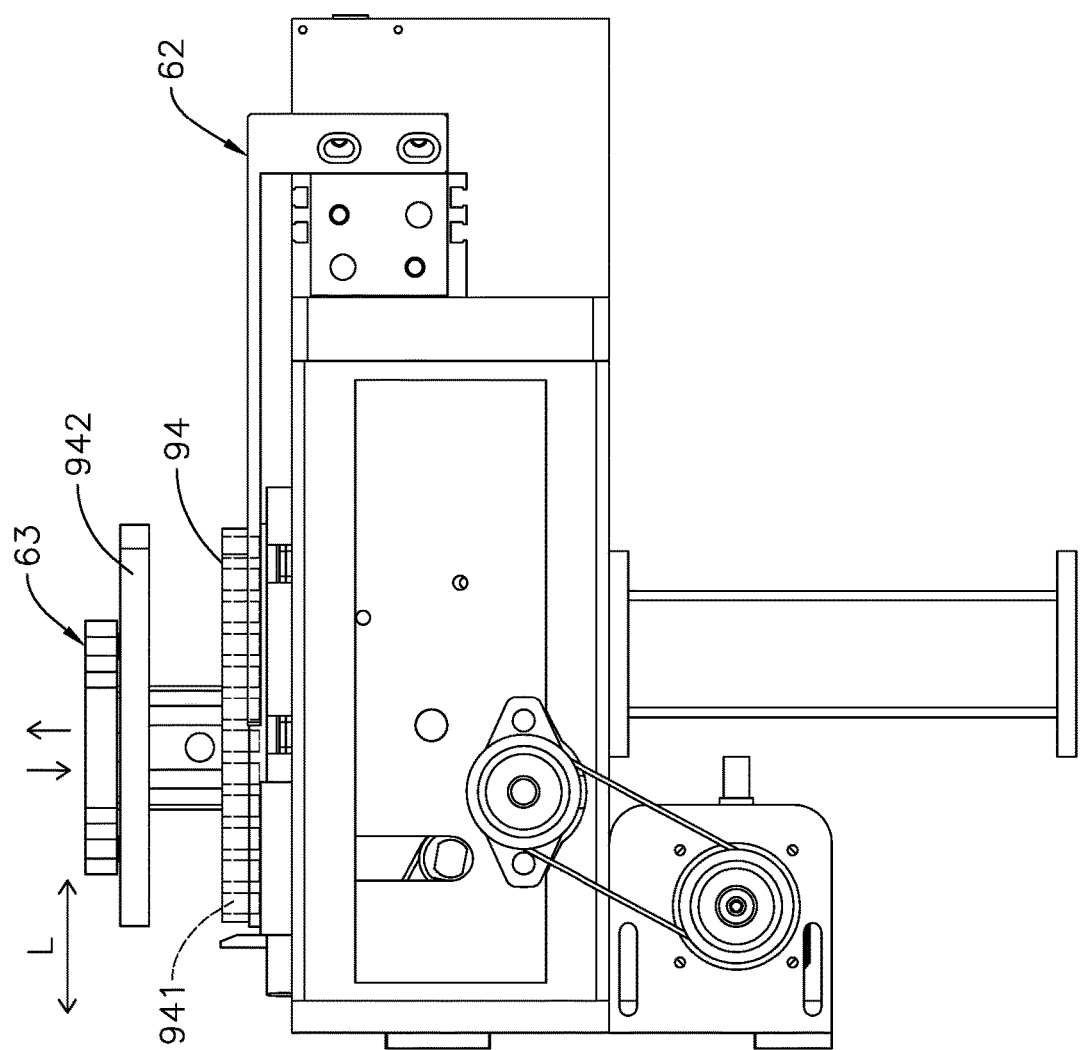
FIGS. 23 and 24 are operational schematic cross sectional views of the cell culture plate positioning mechanism of the cell and medicament dispensing device in FIG. 17, showing operating statuses of a lid opener of the cell culture plate positioning mechanism.

With reference to FIGS. 23 and 24, the lid opener 63 is mounted above the positioning seat 61. The lid opener 63 is capable of moving upward and downward, and is capable of moving sideways. The lid opener 63 is movable to a position above the cell culture plate 94. The suction cups 64 are mounted on a bottom surface of the lid opener 63 and are configured to adhere to the upper lid 942 of the cell culture plate 94. In the preferred embodiment, the suction cups 64 are connected to a vacuum generator (not shown in figures) such that the suction cups 64 are adhered to the upper lid 942 by vacuum pressure. In another preferred embodiment, one suction cup 64 is sufficient for adhering to the upper lid 942.

Figure 19:
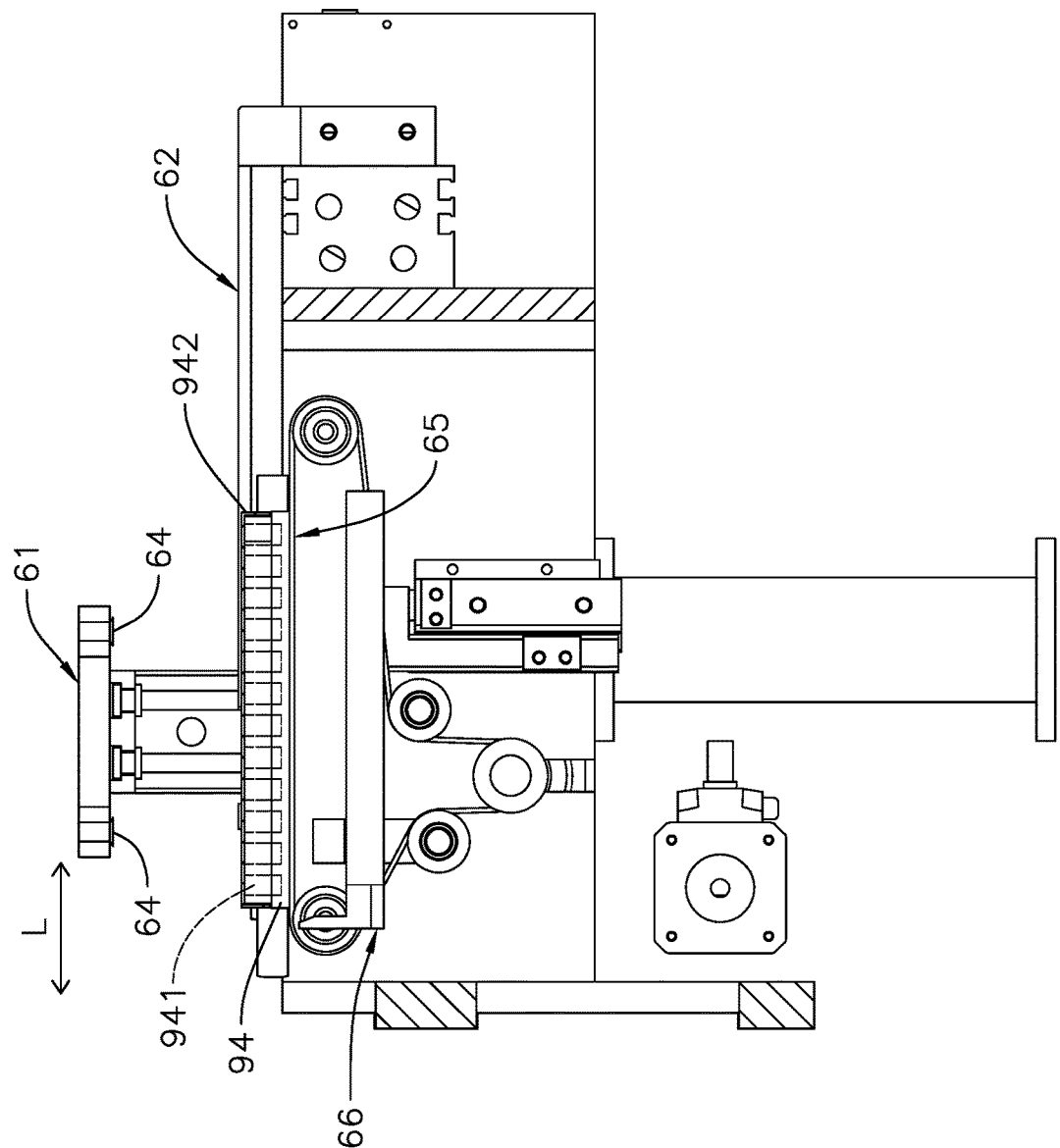
FIGS. 19 and 20 are operational schematic side views of the cell culture plate positioning mechanism of the cell and medicament dispensing device in FIG. 17, showing operating statuses of the cell culture plate positioning mechanism viewed along the transverse direction.
Figure 20:
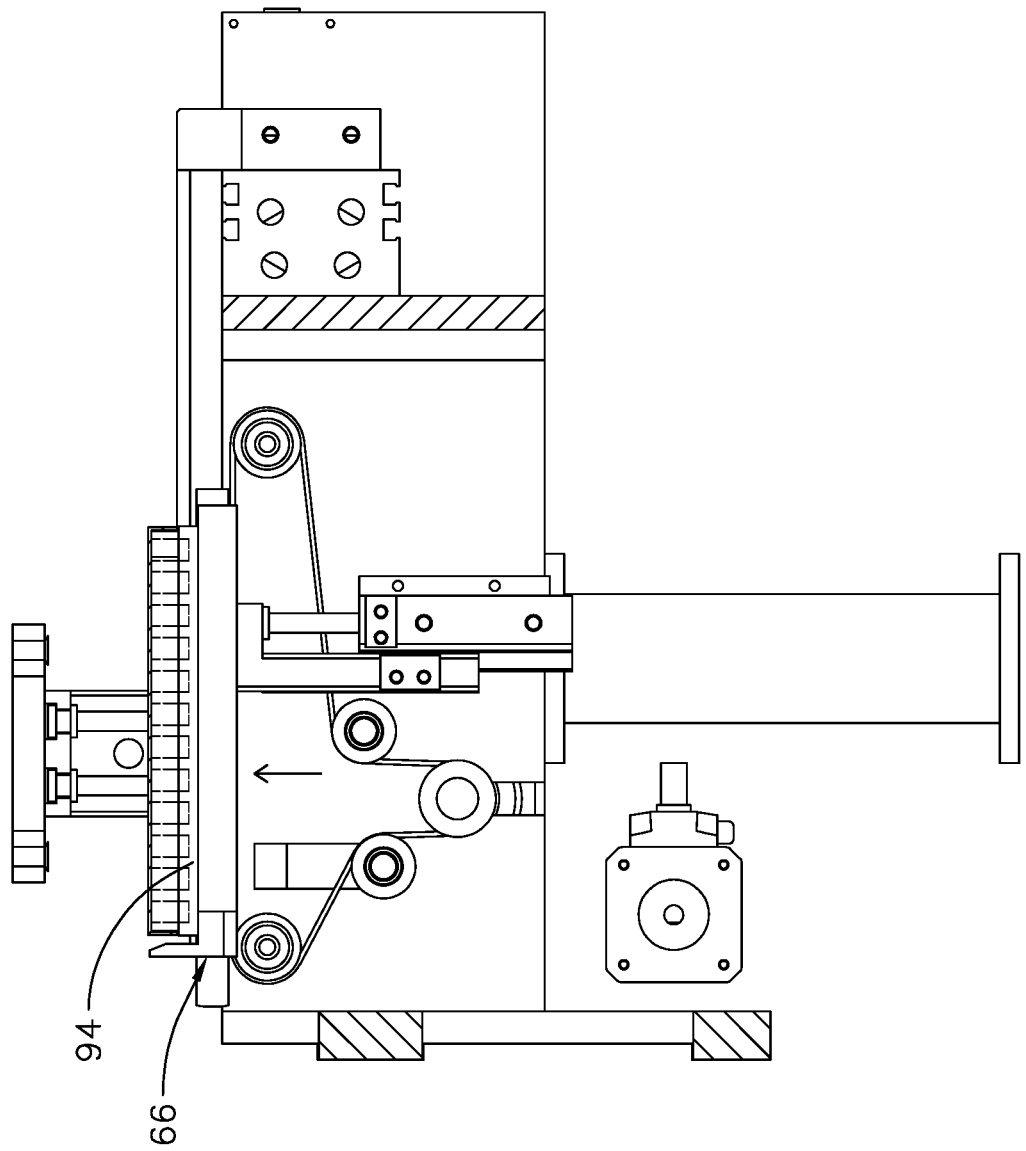

With reference to FIGS. 18 to 20, the cell culture plate transfer module 65 is mounted in the positioning seat 61, and is preferably a pair of parallel conveyer belts. The cell culture plate transfer module 65 is capable of moving the cell culture plate 94 rested on the positioning seat 61 toward or away from the cell culture plate conveyer 50.

The secondary positioning module 66 is mounted in the positioning seat 61, is capable of moving upward or downward, and is configured to lift the cell culture plate 94 rested on the positioning seat 61. When the cell culture plate 94 is lifted by the secondary positioning module 66, two ends of the secondary positioning module 66 attach two opposite sides of the cell culture plate 94 facing toward or moving along with the longitudinal direction L to fix a position of the cell culture plate 94 in the longitudinal direction L.

Detailed operating steps of the cell culture plate positioning mechanism 60 are as described below.

1. The cell culture plate conveyer 50 delivers a ready-to-process cell culture plate 94 to the positioning seat 61. The cell culture plate transfer module 65 roughly adjust a position of the cell culture plate 94 on the positioning seat 61.

2. With reference to FIGS. 19 and 20, the secondary positioning module 66 moves upward to lift the cell culture plate 94 and fix the position of the cell culture plate 94 in the longitudinal direction L.

3. With reference to FIGS. 21 and 22, the primary positioning module 62 clamps the two opposite sides of the cell culture plate 94 that face toward and move longitudinally away from the transverse direction T such that a position of the cell culture plate 94 in the transverse direction T is fixed.

4. With reference to FIG. 23, the lid opener 63 moves downward to adhere to the upper lid 942 with the suction cups 64, and then the lid opener 63 moves upwards to separate the upper lid 942 from the cell culture plate 94.

5. With reference to FIGS. 23 and 24, the lid opener 63 moves sideways away from the position above the cell culture plate 94 to uncover partially the wells 941 of the cell culture plate 94.

Figure 30:
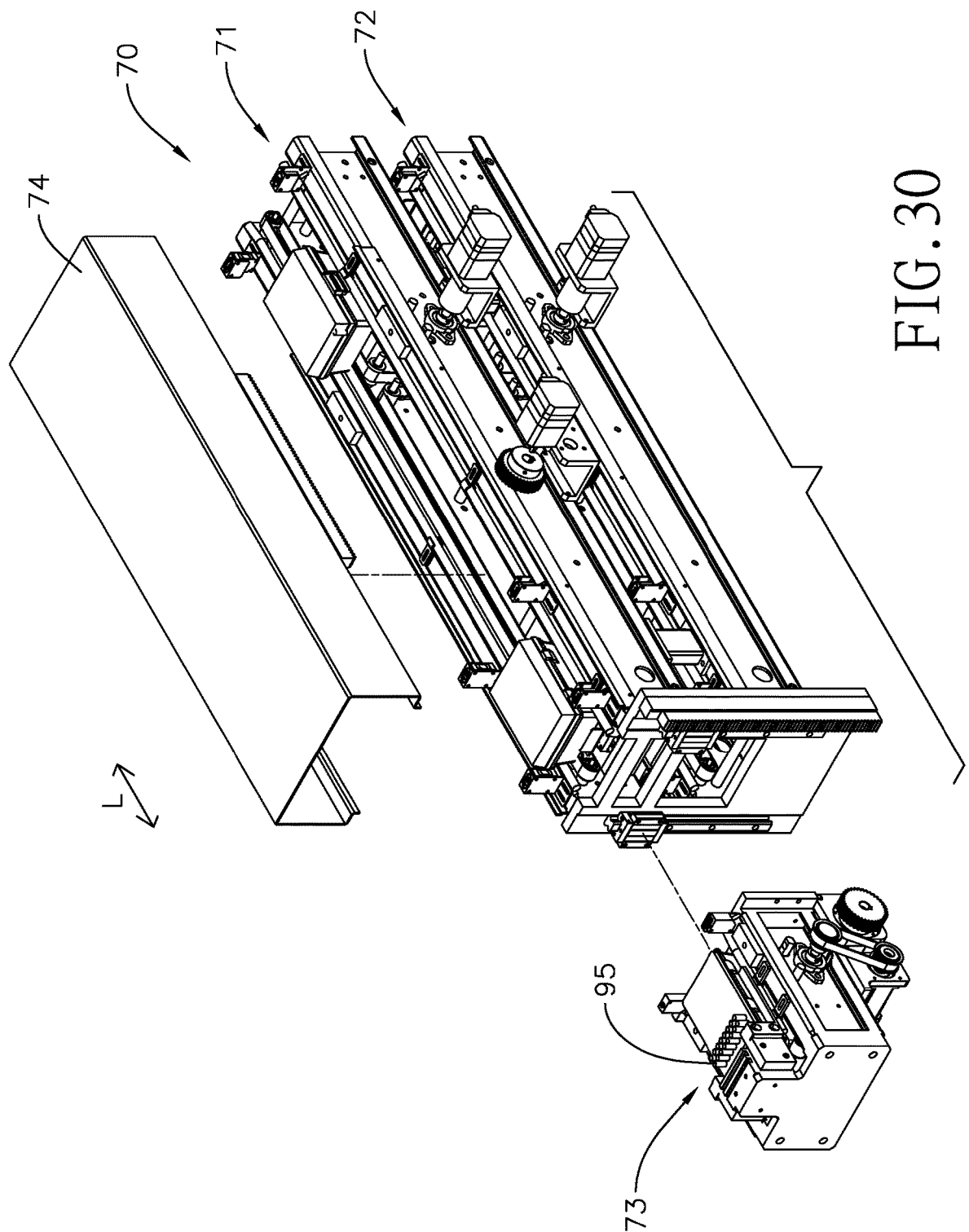
FIG. 30 is an exploded perspective view of a pipette-tip feeder of the cell and medicament dispensing device in FIG. 1.
Figure 31:
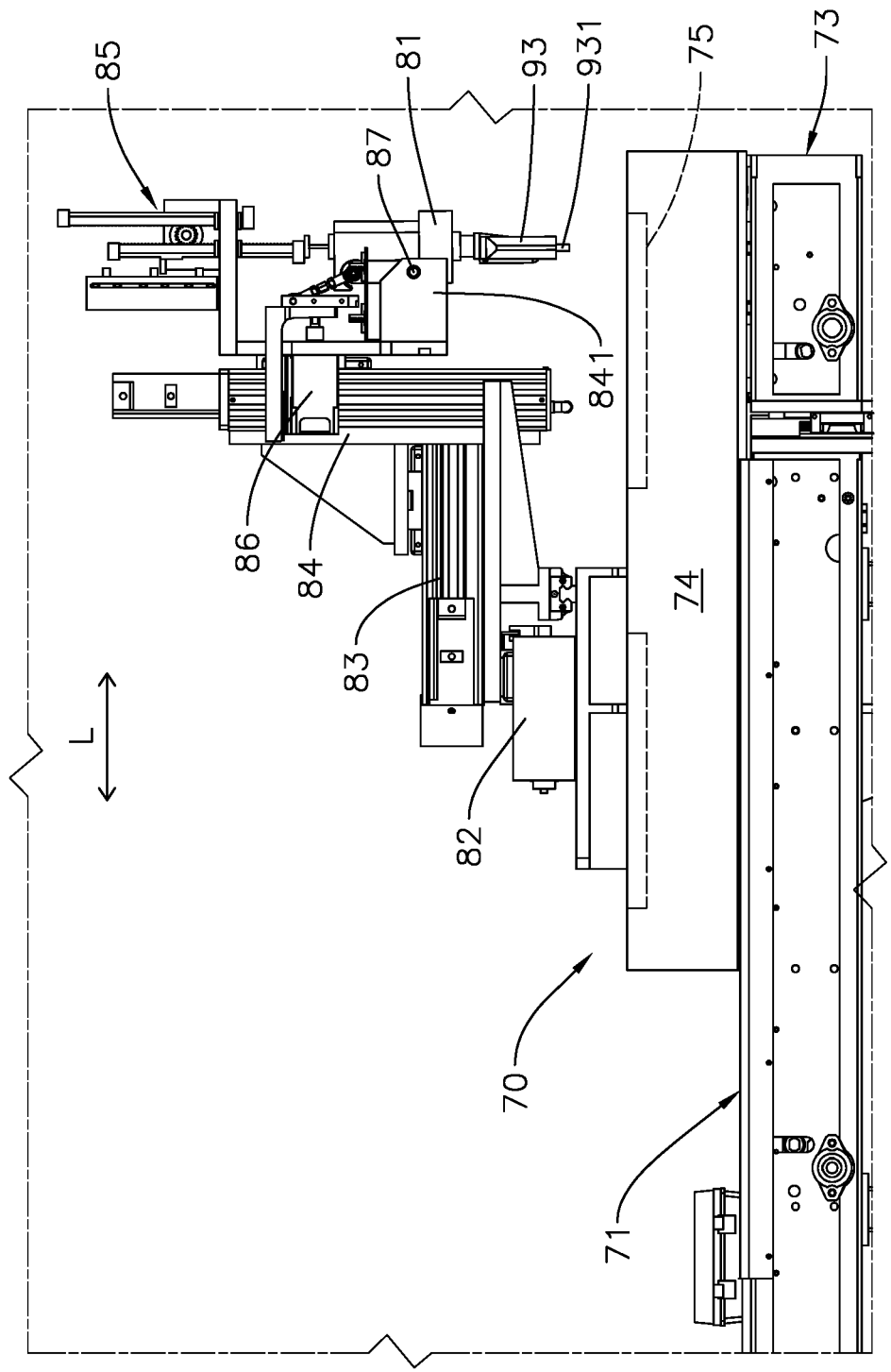
FIGS. 31 and 32 are operational schematic side views of the cell and medicament dispensing device in FIG. 1, showing operating statuses of the dispensing mechanism and the pipette-tip feeder along the transverse direction.

With reference to FIGS. 30 to 32, the pipette-tip feeder 70 is mounted on the base 10 and configured to deliver pipette-tips 95 packed in boxes. The pipette-tip feeder 70 has an input conveyer belt 71, an output conveyer belt 72, a tip positioning module 73, a sliding tip cover 74, and at least one UV lamp 75.

The tip positioning module 73 is mounted on an end of the input conveyer belt 71. The output conveyer belt 72 is mounted under the input conveyer belt 71. The output conveyer belt 72 and the input conveyer belt 71 operate in opposite directions. The tip positioning module 73 is capable of moving downward to align with an end of the output conveyer belt 72. The input conveyer belt 71 is configured to deliver unused pipette-tips 95 packed in boxes to the tip positioning module 73, and then the tip positioning module 73 fine-tunes a position of the pipette-tip 95 for other mechanism of the present invention.

The sliding tip cover 74 is movably mounted on the input conveyer belt 71 and is movable to a position above the tip positioning module 73 to cover partially the pipette-tips 95 in use, thereby preventing the pipette-tips 95 unused yet from being contaminated. At least one UV lamp 75 is mounted in an inner surface of the sliding tip cover 74 to maintain the unused pipette-tips 95 in a sterilized condition with ultraviolet irradiation.

Figure 26:
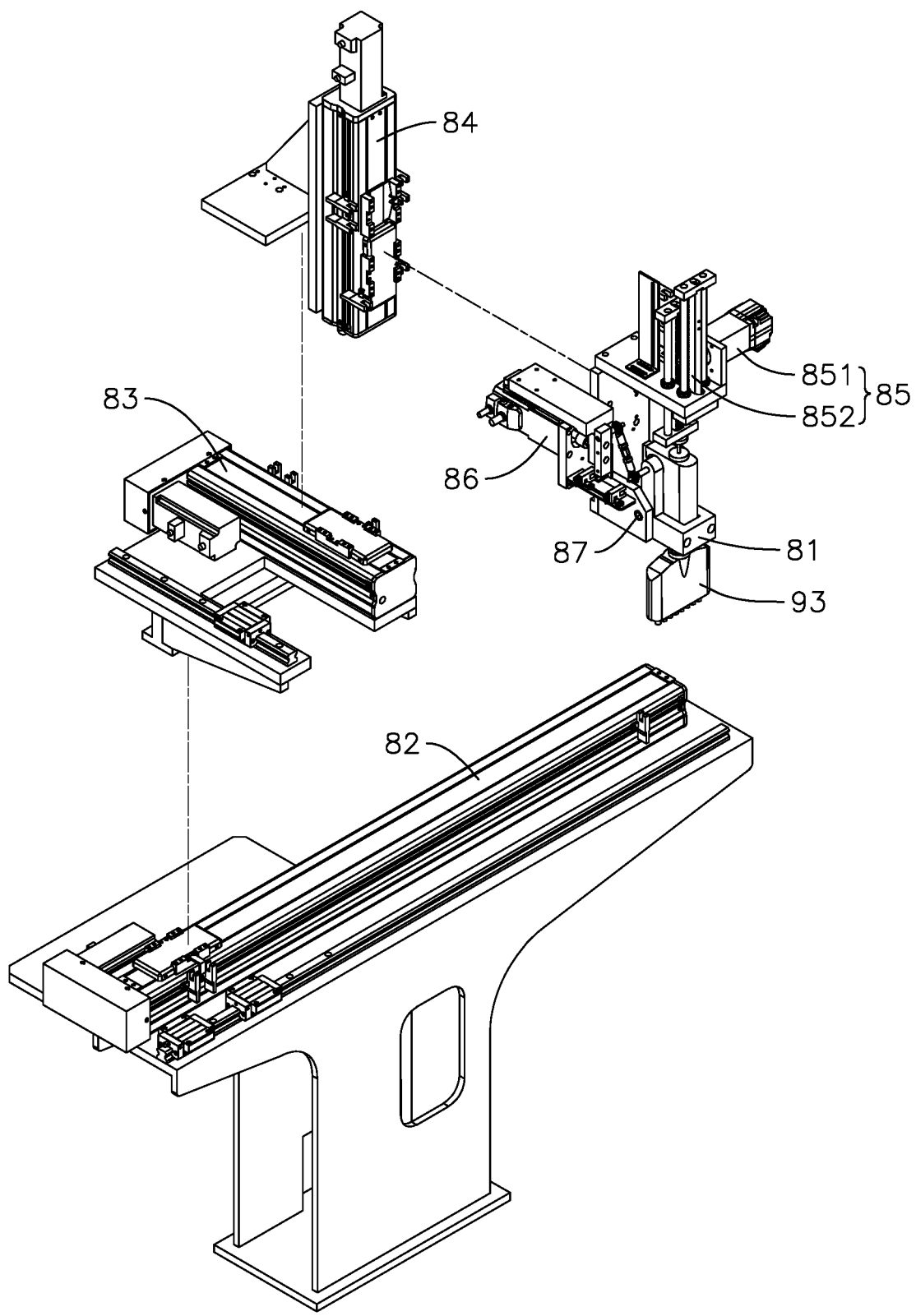
FIG. 26 is an exploded perspective view of the dispensing mechanism of the cell and medicament dispensing device in FIG. 25.
Figure 27:
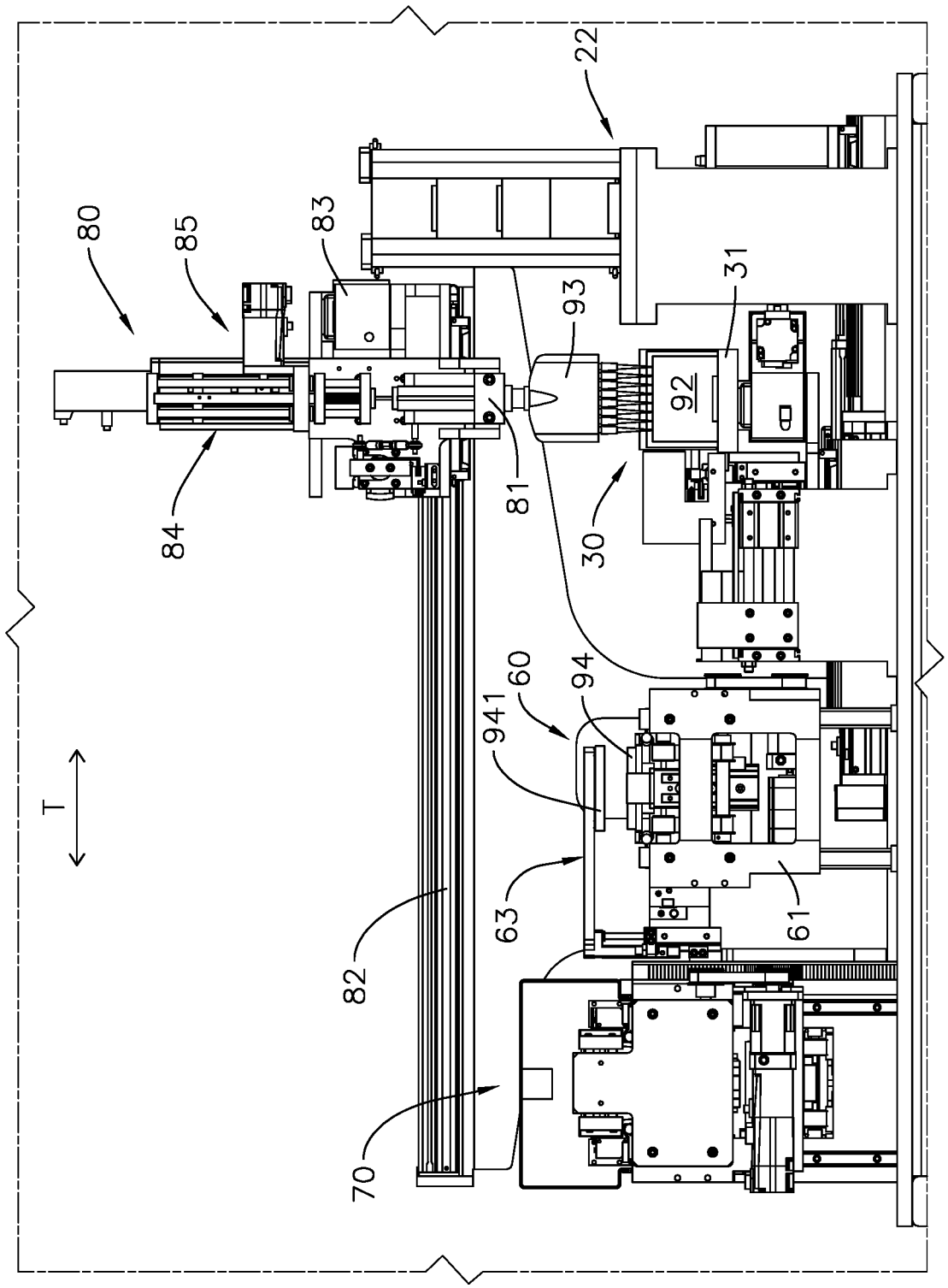
FIGS. 27 to 29 are operational schematic side views of the cell and medicament dispensing device in FIG. 1, showing operating statuses of the dispensing mechanism viewed along the longitudinal direction.
Figure 28:
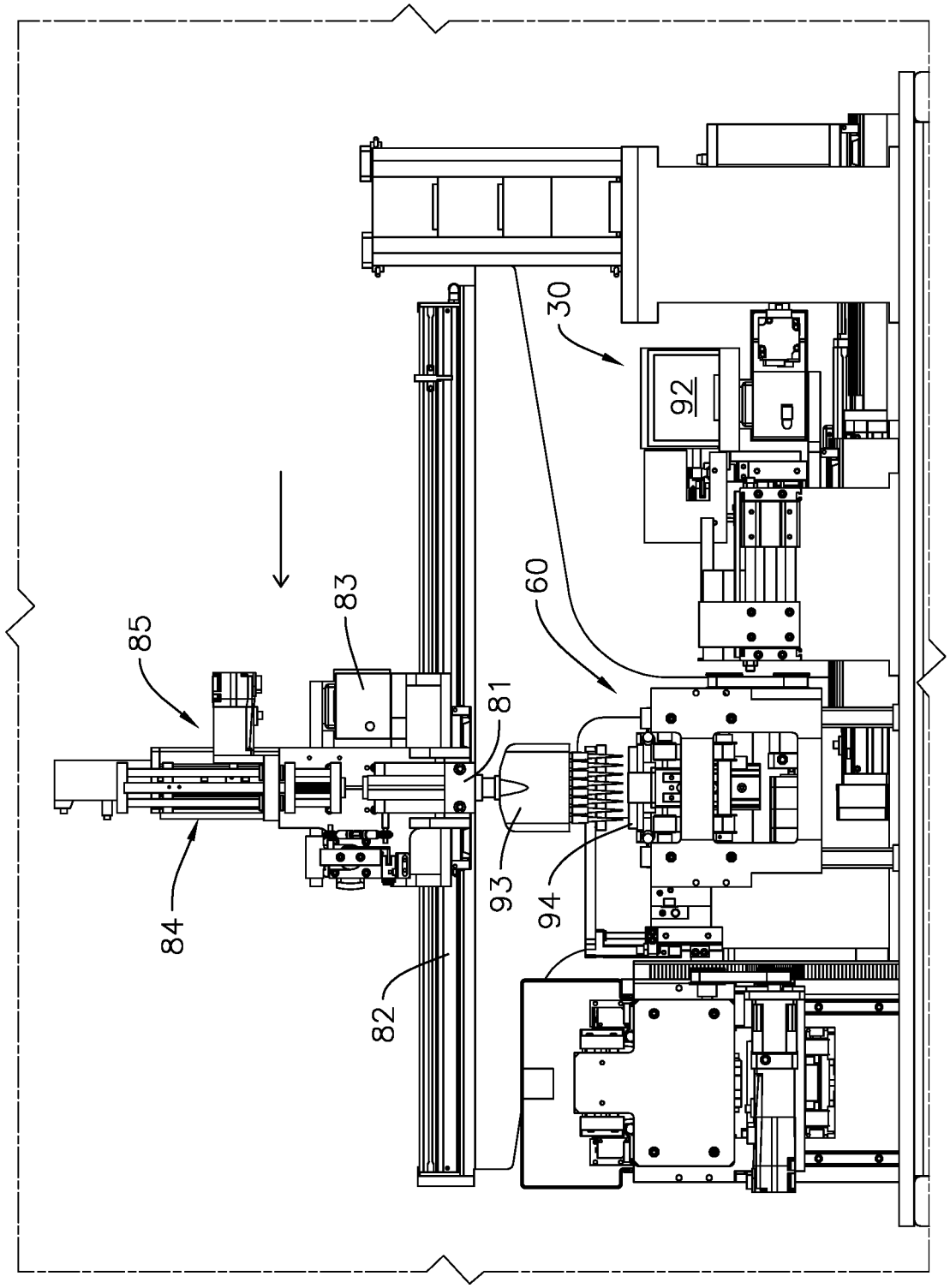

With reference to FIGS. 25 to 27, the dispensing mechanism 80 is mounted on the base 10. The dispensing mechanism 80 has a dispensing seat 81. In the preferred embodiment, the dispensing mechanism 80 further has a first dispensing linear module 82, a second dispensing linear module 83, a third dispensing linear module 84, a tip ejector 85, a tilt actuator 86, and a pivot axle 87.

The dispensing seat 81 is configured to fix the pipette 93 and configured to control aspirate and discharge operation of the pipette 93. The dispensing seat 81 is movable relative to the base 10 and is movable back and forth between a position above the dispensing area 103 of the base 10 and a position above the cell culture plate positioning mechanism 60. When the dispensing seat 81 is above the dispensing area 103, the dispensing seat 81 is configured to insert the pipette 93 with the at least one pipette-tip 95 into any one of the solution recesses 921 of the transfer plate 92 and execute the aspirate operation of the pipette 93 to draw up liquid inside the solution recess 921. When the dispensing seat 81 is above the cell culture plate positioning mechanism 60, the dispensing seat 81 executes the discharge operation of the pipette 93 to release the liquid aspired in the at least one pipette-tip 95 into one of the wells 941 of the cell culture plate 94.

In the preferred embodiment, the dispensing seat 81 moves and inserts the pipette-tip 95 into the wells 941 via the first dispensing linear module 82, the second dispensing linear module 83, and the third dispensing linear module 84. To be specific, the first dispensing linear module 82 is mounted on the base and extends in the transverse direction T. The second dispensing linear module 83 is mounted on the first dispensing linear module 82 and extends in the longitudinal direction L. The third dispensing linear module 84 is mounted on the second dispensing linear module 83 and extends in vertical direction. The dispensing seat 81 is mounted on the third dispensing linear module 84. As a result, the dispensing seat 81 has 3 degrees of freedom via the dispensing linear modules 82, 83, and 84.

Additionally, the dispensing seat 81 in this embodiment is movable to a position above the tip positioning module 73 of the pipette-tip feeder 70, and then the dispensing seat 81 is movable toward the tip positioning module 73 to connect with the new pipette-tips 95. Furthermore, the dispensing seat 81 is pivotally mounted on the base 10. Rotation of the dispensing seat 81 relative to the base 10 is capable of aligning the tip connectors 931 of the pipette 93 with pipette-tips 95 on the tip positioning module 73 such that the centerline of the tip connectors 931 are parallel to the centerline of the pipette-tips 95; the rotation of the dispensing seat 81 relative to the base 10 is also capable of making the centerline of the tip connectors 931 inclined to the centerline of the pipette-tips 95.

Figure 33:
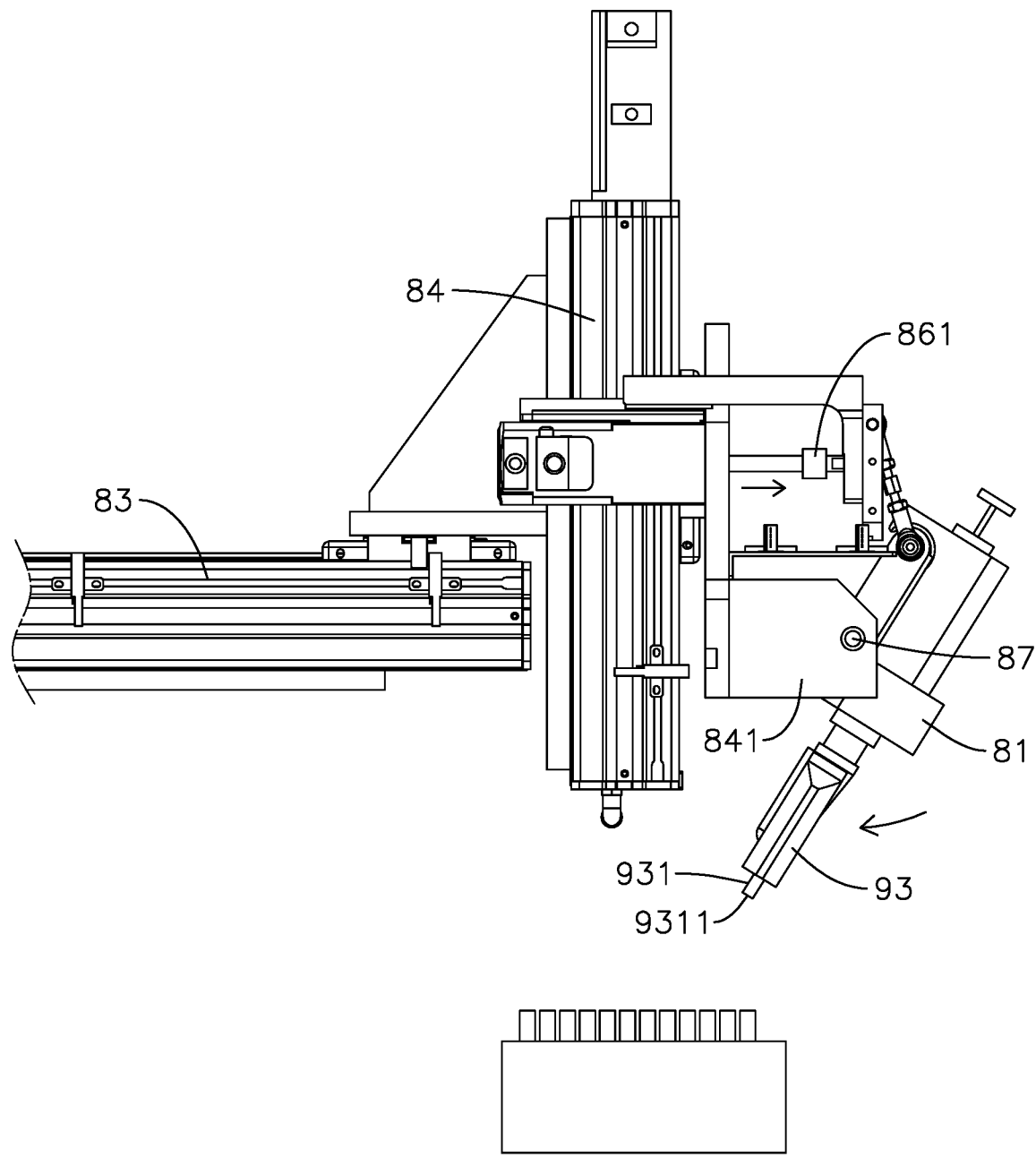
FIGS. 33 to 36 are operational schematic side views of the cell and medicament dispensing device in FIG. 1, showing operating statuses for replacing pipette-tips viewed along the transverse direction.

With reference to FIGS. 25, 32, and 33, to be precise, the dispensing seat 81 is pivotally mounted on a connecting seat 841 of the third dispensing linear module 84 via the pivot axle 87, and the pivot axle 87 is nonparallel to the tip connectors 931. To be more precise, the pivot axle 87 substantially extends in the transverse direction T, and the pivot axle 87 is substantially perpendicular to the tip connectors 931. As a result, the rotation of the dispensing seat 81 is capable of adjusting the centerline of the tip connectors 931 by the vertical line; it means that the rotation of the dispensing seat 81 is also capable of tilting the tip connectors 931 such that the centerline of the tip connectors 931 form an adjustable angle with the vertical line.

In the preferred embodiment, the tilt actuator 86 is a linear actuator mounted on the connecting seat 841. A shaft 861 of the tilt actuator 86 is connected to the dispensing seat 81 to control a rotating angle of the dispensing seat 81 around the pivot axle 87.

The tip ejector 85 is mounted on the dispensing seat 81 and configured to press against the pipette 93 to remove the pipette-tip 95 from the pipette 93. With reference to FIG. 26, the tip ejector 85 has a motor 851 and a rack 852, and the motor 851 drives the rack 852 to press against a release button (not shown in figures) on the pipette 93 to remove the pipette-tip 95 from the pipette 93.

Coordination between the pipette-tip feeder 70 and the dispensing mechanism 80 makes automatic replacement of the pipette-tips 95 possible, and detailed operating steps are as described below.

1. The tip ejector 85 presses against the release button on the pipette 93 to remove the pipette-tips 95 from the pipette 93.

Figure 29:
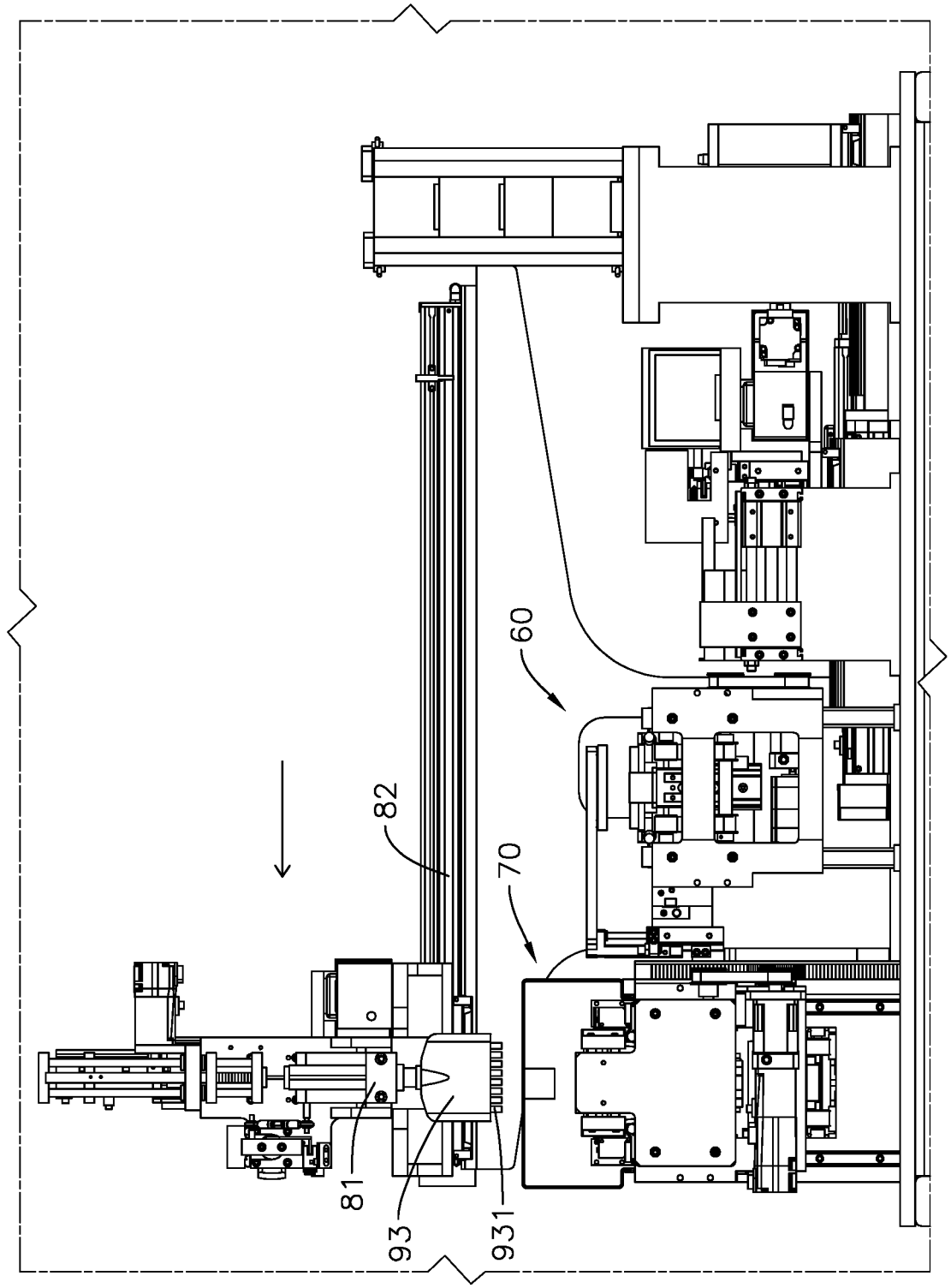

2. With reference to FIGS. 29 and 31, the dispensing seat 81 moves to the position above the tip positioning module 73.

3. With reference to FIG. 32, the sliding tip cover 74 moves oppositely away from the tip positioning module 73 to reveal the pipette-tips 95 on the tip positioning module 73.

4. With reference to FIG. 33, the dispensing seat 81 is tilted by the tilt actuator 86 such that the centerline of the tip connectors 931 form an angle with the vertical line.

Figure 34:
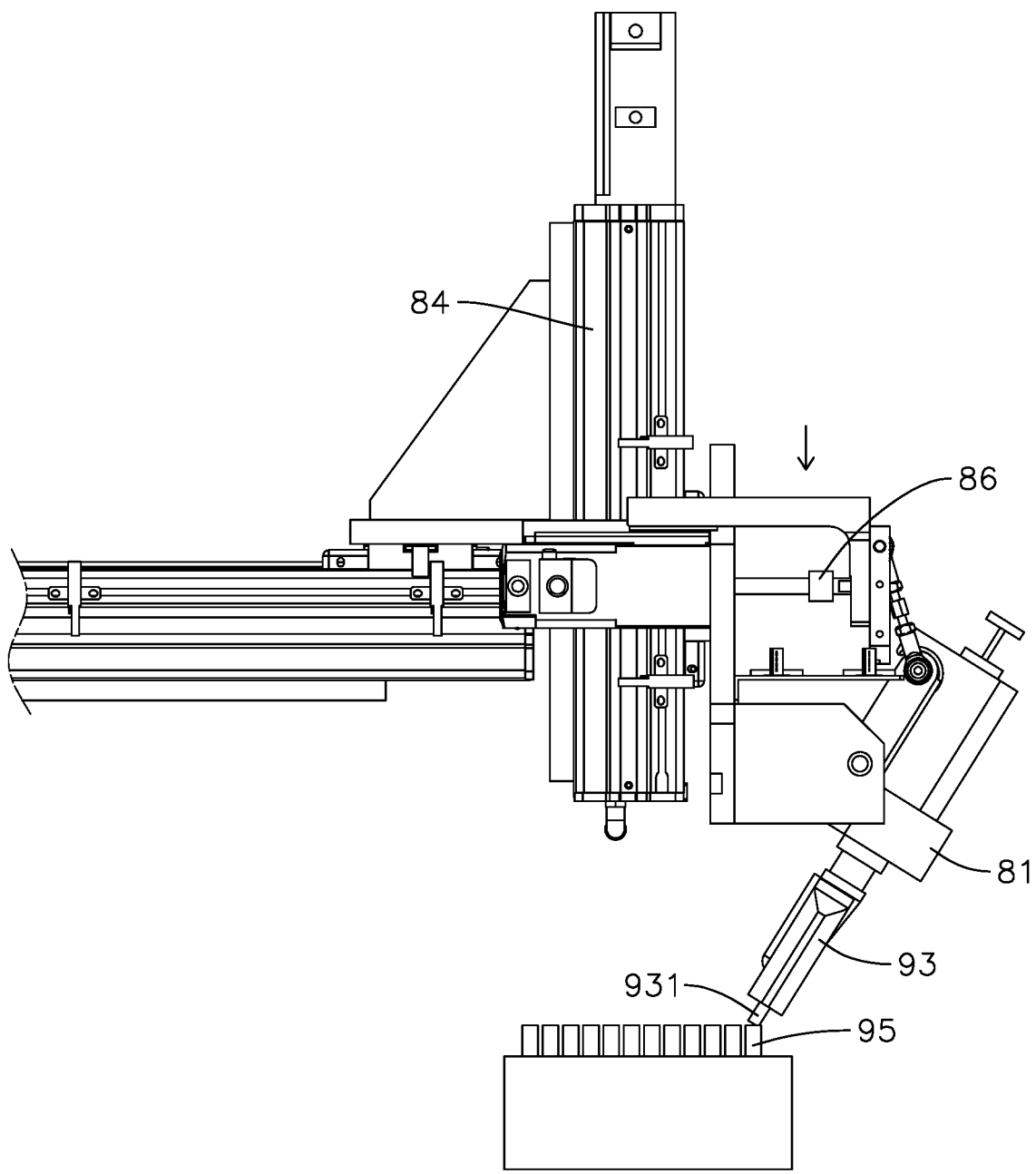

5. With reference to FIGS. 33 and 34, the dispensing seat 81 moves downward to partially insert a distal end 9311 (as shown in FIG. 33) of each of the tip connectors 931 into a respective one of the pipette-tips 95.

Figure 35:
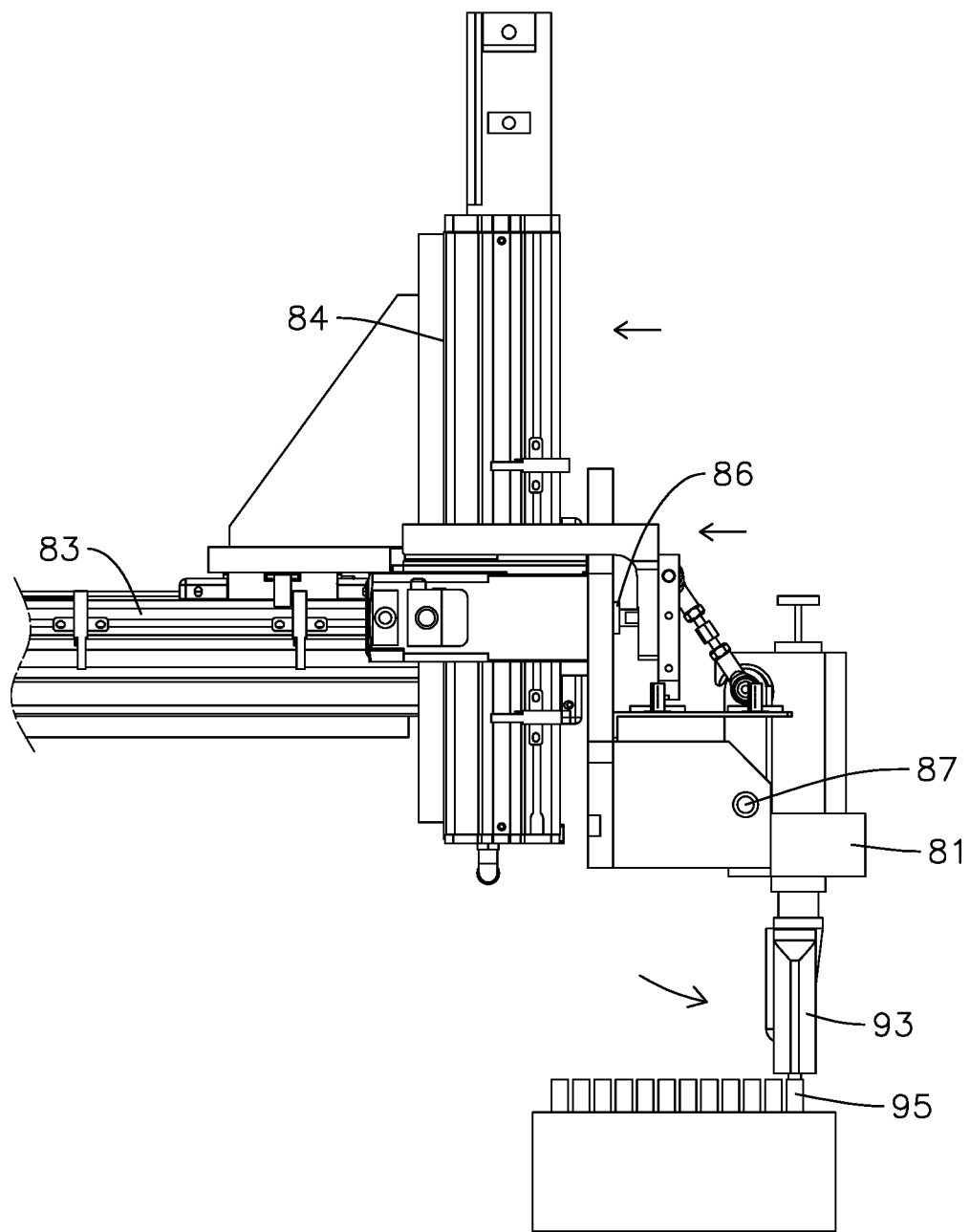
Figure 36:
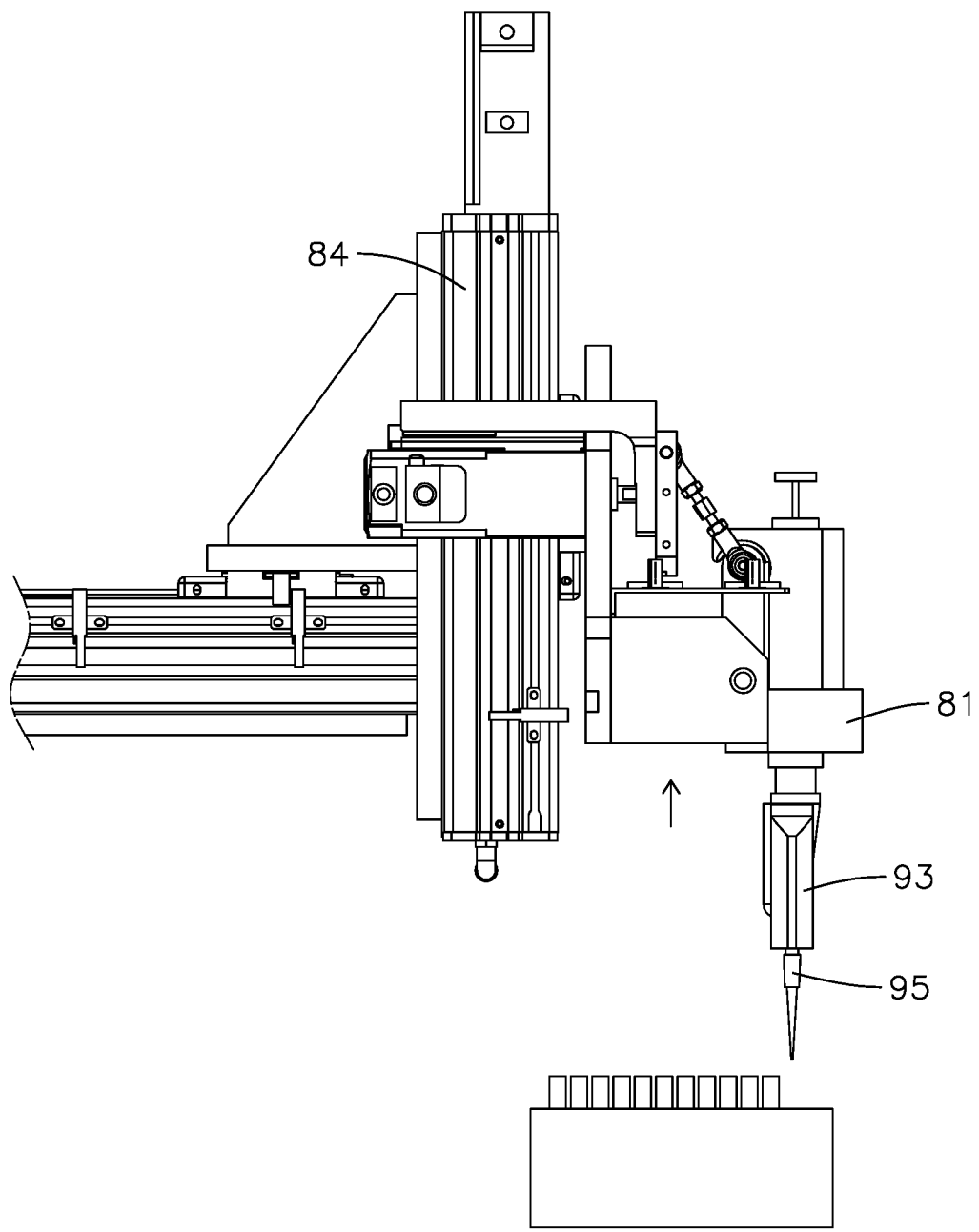

6. With reference to FIGS. 35 and 36, the tilt actuator 86 gradually straightens the dispensing seat 81 to align the centerline of the tip connectors 931 to match with the vertical line again. In the meantime, the dispensing linear modules 82, 83, and 84 drive the dispensing seat 81 to gradually press the tip connectors 931 against the pipette-tips 95 such that the tip connectors 931 are eventually connected with the pipette-tips 95, and then the dispensing seat 81 moves upward to continue dispensing operation.

Figure 37:
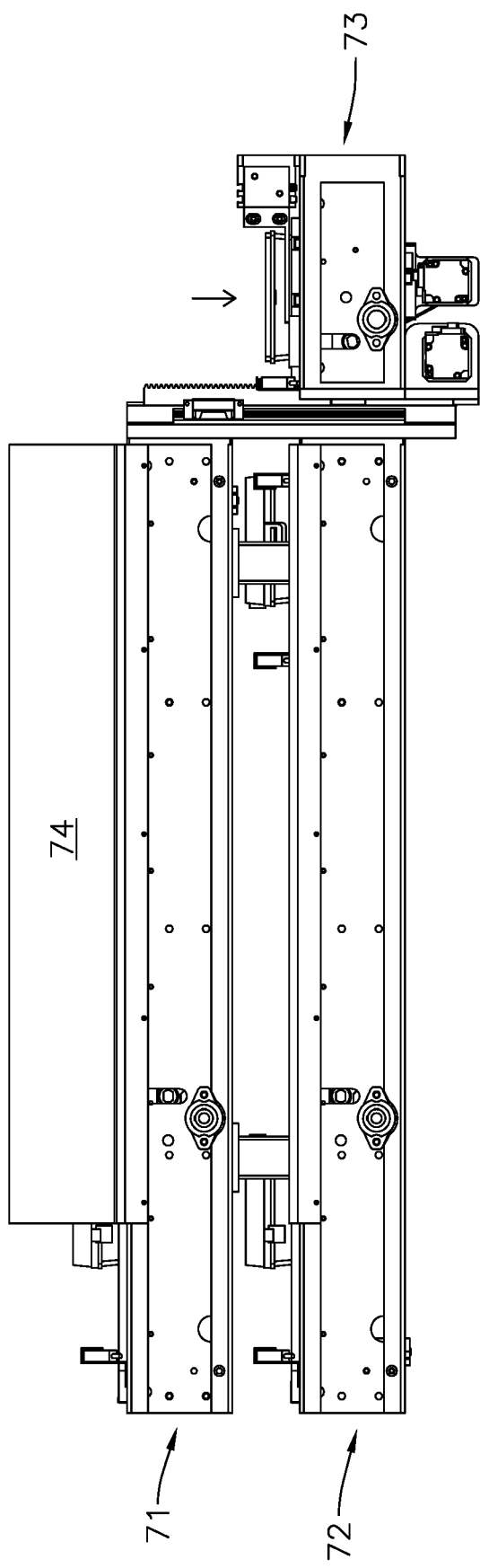
FIG. 37 is a schematic side view of the cell and medicament dispensing device in FIG. 1, showing a tip positioning module of the pipette-tip feeder being capable of moving upward and downward.

7. With reference to FIG. 37, when the pipette-tips 95 delivered in a box have been depleted, the tip positioning module 73 moves downward to align with the end of the output conveyer belt 72 to send away the empty box using the output conveyer belt 72.

The box retriever for the box of pipette-tips 95 is substantially similar to the transfer plate serving mechanism 21 aforementioned. The difference between the transfer plate retriever 22 and the transfer plate serving mechanism 21 is that the transfer plate retriever 22 is configured to recycle used transfer plates 92, and therefore operating procedure of the transfer plate retriever 22 is in a reverse order compared with the transfer plate serving mechanism 21. That is, the transfer plate retriever 22 detaches the used transfer plates 92 with the transfer plate positioning mechanism 30, and then stacks the used transfer plates 92 in a bottom-up way.

Figure 38:
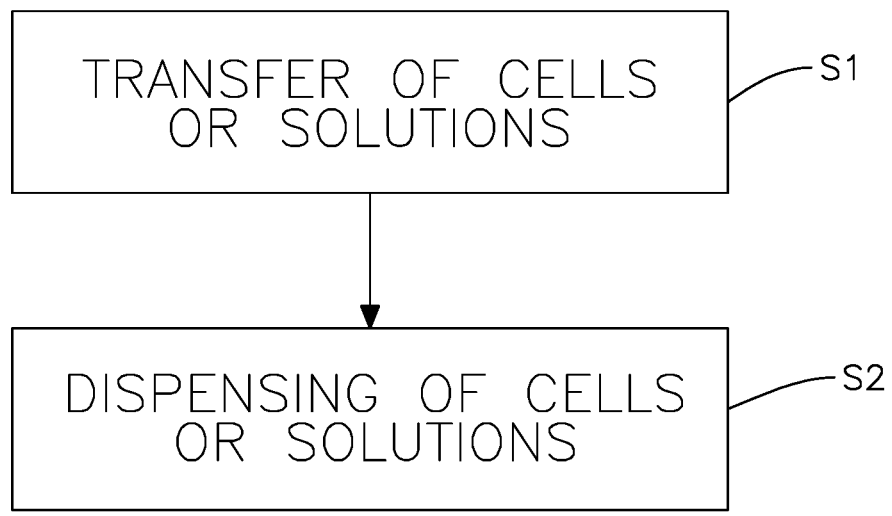
FIG. 38 is a flow chart of a cell and medicament dispensing method for drug screening in accordance with the present invention.

With reference to FIG. 38, a cell and medicament dispensing method for drug screening in accordance with the present invention comprises the following steps: the first step (S1) is transfer of cells or solutions; the second step (S2) is dispensing of cells or solutions. The cell and medicament dispensing method is performed by the aforementioned cell and medicament dispensing device, but not limited thereto.

The first step (S1) is transfer of cells or solutions. With reference to FIGS. 10 to 15, the plate feeder 213 of the transfer plate serving mechanism 21 moves the transfer plate 92 to the transfer plate entrance area 101 on the base 10. The transfer plate 92 has multiple solution recesses 921 as aforementioned. The positioning slider 31 of the transfer plate positioning mechanism 30 moves to the transfer plate entrance area 101 and connects with the transfer plate 92. The positioning slider 31 moves the transfer plate 92 to the receiving area 102 of the base 10.

With reference to FIGS. 3, 6, and 15, the injection mechanism 40 injects multiple solutions 91 into the solution recesses 921 of the transfer plate 92. Each of the solution recesses 921 may be injected with one single solution 91, or may be injected with multiple kinds of the solutions 91. Each of the solutions 91 comprises one single type of medicament or cells. In the preferred embodiment, the sliding plate-cover 34 partially covers the openings of the solution recesses 921 to prevent foreign objects from falling into the unused part of solution recesses 921.

With reference to FIGS. 8 and 9, multiple spare transfer plates 96 can be stacked on the transfer plate serving mechanism 21. After the plate feeder 213 moves the transfer plate 92 to the transfer plate entrance area 101 of the base 10, the transfer plate serving mechanism 21 moves the bottommost spare transfer plate 96 to the plate feeder 213. By moving the bottommost spare transfer plate 96 first, risk of foreign objects falling into the spare transfer plate 96 is minimized.

In the preferred embodiment, the plate-locking clamps 212 first move away from each other, allowing the spare transfer plate 96 to drop down. In the meantime, the plate lifting actuator 214 moves upward and protrudes through the plate lifting opening 2131 such that only the bottommost spare transfer plate 96 is located under the plate dropping opening 2111, keeping the other spare transfer plates 96 still above the plate dropping opening 2111. Then, the plate-locking clamps 212 move toward each other to prevent the other spare transfer plates 96 from dropping through the plate dropping opening 2111, and then the plate lifting actuator 214 moves downward to its original position such that the bottommost spare transfer plate 96 can stay and fix on the plate feeder 213.

Figure 14:
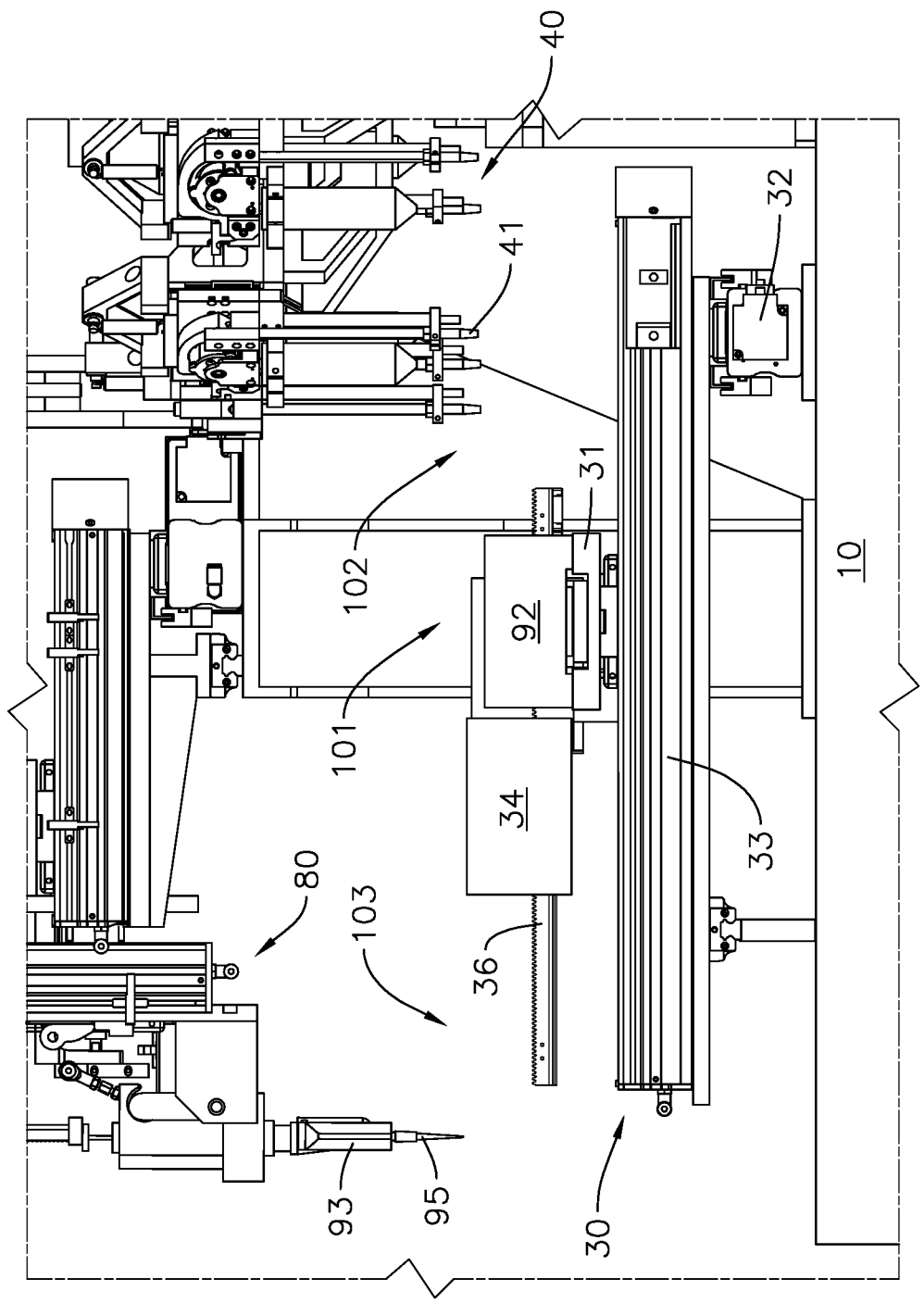
FIGS. 14 to 16 are operational schematic side views of the cell and medicament dispensing device in FIG. 1, showing operating statuses of the transfer plate positioning mechanism and an injection mechanism.

The second step (S2) is dispensing of cells or solutions. With reference to FIGS. 14 to 16, the positioning slider 31 moves the transfer plate 92 to the dispensing area 103 on the base 10. The cell culture plate 94 has multiple wells 941 as aforementioned. The dispensing mechanism 80 moves the pipette 93 back and forth between the position above the dispensing area 103 and the position above the cell culture plate 94 to dispense liquid in each of the solution recesses 921 of the transfer plate 92 into the wells 941 of the cell culture plate 94.

In the preferred embodiment, the sliding plate-cover 34 moves away from the transfer plate 92 to uncover one of the openings of the solution recesses 921. After the pipette 93 dispenses liquid in said one of the openings of the solution recesses 921, the sliding plate-cover 34 moves back toward the transfer plate 92 to cover fully the openings of the solution recesses 921 again.

In summary, by coordination among the transfer plate serving mechanism 21, the transfer plate positioning mechanism 30, and the injection mechanism 40, liquids and cells for drug screening are automatically transferred to the solution recesses 921 of the transfer plate 92. Afterwards, liquid in each of the solution recesses 921 is automatically dispensed into the wells 941 of the cell culture plate 94 by coordination between the transfer plate positioning mechanism 30 and the dispensing mechanism 80. As a result, the process of drug screening is automated to reduce labor and improve quality significantly.

Even though numerous characteristics and advantages of the present invention have been set forth in the foregoing description, together with details of the structure and features of the invention, the disclosure are illustrative only. Changes may be made in the details, especially in matters of shape, size, and arrangement of parts within the principles of the invention to the full extent indicated by the broad general meaning of the terms in which the appended claims are expressed.

What is claimed is:

1. A cell and medicament dispensing device for drug screening, configured to inject multiple solutions into multiple solution recesses of a transfer plate; then, liquid inside each of the solution recesses dispensed into multiple wells of a cell culture plate with a pipette; at least one pipette-tip detachably connected to a bottom of the pipette; the cell and medicament dispensing device comprising:
   a base having a transfer plate entrance area, a receiving area, and a dispensing area thereon;
   a transfer plate serving mechanism mounted on the base and being adjacent to the transfer plate entrance area; the transfer plate serving mechanism configured to accommodate the transfer plate and being capable of moving the transfer plate to the transfer plate entrance area of the base;
   a transfer plate positioning mechanism mounted on the base and being adjacent to the transfer plate serving mechanism; the transfer plate positioning mechanism having:
      a positioning slider configured to connect with the transfer plate; the positioning slider movably mounted on the base and selectively corresponding in position to the transfer plate entrance area, the receiving area, or the dispensing area; and
      a sliding plate-cover movably mounted on the positioning slider and being movable to a position above the positioning slider to cover openings of the solution recesses of the transfer plate;
   an injection mechanism mounted on the base and being adjacent to the transfer plate positioning mechanism; the injection mechanism having:
      multiple injection heads; each of the injection heads being in fluid communication with a respective one of the solutions and being movable to the receiving area of the base; wherein when one of the injection heads is moved into the receiving area of the base, the positioning slider is configured to align any one of the solution recesses of the transfer plate to said injection head in the receiving area such that said injection head injects one of the solutions into a corresponding one of the solution recesses;
   a cell culture plate positioning mechanism mounted on the base and configured to connect with the cell culture plate; the cell culture plate positioning mechanism having:
      a positioning seat mounted on the base and configured to accommodate the cell culture plate; and
      a primary positioning module mounted on the positioning seat and configured to clamp the cell culture plate; and
   a dispensing mechanism mounted on the base and having:
      a dispensing seat configured to fix the pipette and configured to control aspirate and discharge operation of the pipette; the dispensing seat being movable relative to the base and being movable back and forth between a position above the dispensing area of the base and a position above the cell culture plate positioning mechanism;
   when the dispensing seat is above the dispensing area, the dispensing seat configured to insert the at least one pipette-tip of the pipette into any one of the solution recesses of the transfer plate and execute the aspirate operation of the pipette; and
   when the dispensing seat is above the cell culture plate positioning mechanism, the dispensing seat executes the discharge operation of the pipette to release the liquid aspired in the at least one pipette-tip into one of the wells of the cell culture plate.

2. The cell and medicament dispensing device as claimed in claim 1, wherein
   the cell culture plate has an upper lid detachably covering the wells; and
   the cell culture plate positioning mechanism further has
      a lid opener mounted above the positioning seat; the lid opener being capable of moving upward and downward, and capable of moving sideways; the lid opener being movable to a position above the cell culture plate; and
      at least one suction cup mounted on a bottom surface of the lid opener and configured to adhere to the upper lid of the cell culture plate.

3. The cell and medicament dispensing device as claimed in claim 2, wherein the transfer plate serving mechanism has:
   a plate stacking bracket forming a stacking space; the stacking space configured to accommodate multiple spare transfer plates that are stacked vertically;
   a plate dropping opening formed in a bottom of the plate stacking bracket; the spare transfer plates being capable of dropping through the plate dropping opening;
   two plate-locking clamps; each of the plate-locking clamps mounted on a respective side of two opposite sides of the plate dropping opening; the two plate-locking clamps being capable of moving toward each other to prevent the spare transfer plates from passing through the plate dropping opening;

a plate feeder mounted under the plate dropping opening and configured to receive the transfer plates dropped through the plate dropping opening; the plate feeder being movable to the transfer plate entrance area of the base; the plate feeder having:

a plate lifting opening formed through two opposite sides of the plate feeder;

a plate lifting actuator mounted under the plate lifting opening and being capable of moving upward to protrude through the plate lifting opening.

4. The cell and medicament dispensing device as claimed in claim 3, wherein the positioning slider of the transfer plate positioning mechanism is capable of moving upward and downward; and when the positioning slider corresponds in position to the transfer plate entrance area, the plate feeder of the transfer plate serving mechanism is movable to a position above the positioning slider, and the positioning slider is capable of moving upward to protrude through the plate lifting opening.

5. The cell and medicament dispensing device as claimed in claim 1, wherein the transfer plate serving mechanism has:

a plate stacking bracket forming a stacking space; the stacking space configured to accommodate multiple spare transfer plates that are stacked vertically;

a plate dropping opening formed in a bottom of the plate stacking bracket; the spare transfer plates being capable of dropping through the plate dropping opening;

two plate-locking clamps; each of the plate-locking clamps mounted on a respective side of two opposite sides of the plate dropping opening; the two plate-locking clamps being capable of moving toward each other to prevent the spare transfer plates from passing through the plate dropping opening;

a plate feeder mounted under the plate dropping opening and configured to receive the transfer plates dropped through the plate dropping opening; the plate feeder being movable to the transfer plate entrance area of the base; the plate feeder having:

a plate lifting opening formed through two opposite sides of the plate feeder;

a plate lifting actuator mounted under the plate lifting opening and being capable of moving upward to protrude through the plate lifting opening.

6. The cell and medicament dispensing device as claimed in claim 5, wherein the positioning slider of the transfer plate positioning mechanism is capable of moving upward and downward; and when the positioning slider corresponds in position to the transfer plate entrance area, the plate feeder of the transfer plate serving mechanism is movable to a position above the positioning slider, and the positioning slider is capable of moving upward to protrude through the plate lifting opening.

* * * * *